(12) United States Patent
Myers

(10) Patent No.: US 7,824,363 B2
(45) Date of Patent: Nov. 2, 2010

(54) HANDS-FREE BREAST PUMP WITH BALANCED RECIPROCATING DRIVE

(75) Inventor: Kenneth E. Myers, Marietta, GA (US)

(73) Assignee: Medela Holding AG, Baar (CH)

( * ) Notice: Subject to any disclaimer, the term of this patent is extended or adjusted under 35 U.S.C. 154(b) by 132 days.

(21) Appl. No.: 12/114,186

(22) Filed: May 2, 2008

(65) Prior Publication Data

US 2008/0275386 A1 Nov. 6, 2008

Related U.S. Application Data

(60) Provisional application No. 60/915,937, filed on May 4, 2007.

(51) Int. Cl.
*A61M 1/06* (2006.01)
(52) U.S. Cl. .......................... 604/74; 604/73
(58) Field of Classification Search .................. 604/74, 604/73
See application file for complete search history.

(56) References Cited

U.S. PATENT DOCUMENTS

| | | | |
|---|---|---|---|
| 4,857,051 A | 8/1989 | Larsson | |
| 4,941,433 A | 7/1990 | Hanauer | |
| 4,964,851 A * | 10/1990 | Larsson | 604/74 |
| 5,358,476 A | 10/1994 | Wilson | |
| 5,571,084 A | 11/1996 | Palmer | |
| 5,590,648 A | 1/1997 | Mitchell et al. | |
| 5,676,525 A | 10/1997 | Berner et al. | |
| 5,680,978 A | 10/1997 | Pinion | |
| 5,776,098 A | 7/1998 | Silver et al. | |
| 6,110,140 A | 8/2000 | Silver | |
| 6,328,082 B1 | 12/2001 | Lafond | |
| 6,427,475 B1 | 8/2002 | DeFelice et al. | |
| 6,440,100 B1 | 8/2002 | Prentiss | |
| 6,461,324 B1 | 10/2002 | Schlensog | 604/74 |
| 6,547,756 B1 | 4/2003 | Greter et al. | |
| 2001/0044593 A1 * | 11/2001 | Lundy | 604/74 |
| 2002/0062103 A1 | 5/2002 | Larsson et al. | |
| 2002/0156419 A1 | 10/2002 | Silver et al. | 604/74 |
| 2002/0193731 A1 * | 12/2002 | Myers et al. | 604/74 |
| 2003/0069536 A1 | 4/2003 | Greter et al. | |
| 2004/0127845 A1 | 7/2004 | Renz et al. | |
| 2005/0085768 A1 * | 4/2005 | Greter et al. | 604/74 |

FOREIGN PATENT DOCUMENTS

WO    WO 99/44650    9/1999

\* cited by examiner

*Primary Examiner*—Nicholas D Lucchesi
*Assistant Examiner*—Leah Stohr
(74) *Attorney, Agent, or Firm*—McDonell Boehnen Hulbert & Berghoff LLP

(57) ABSTRACT

A hands-free breast pump that includes a balanced push-pull reciprocating drive system that applies pumping force to a vacuum chamber formed by a breast interface cup during inward and outward pump strokes. The breast pump includes a breast cup that has a resilient bellows structure that partially collapses the volume of the vacuum chamber during the inward stroke and recovers the volume of the vacuum chamber during the outward stroke. The pump mechanism includes a cam drive system that translates rotary electric motor power into reciprocating linear action of an actuator arm that drives the bellows structure. The bellows structure acts like a spring that charges (resists the pump force) during the inward stroke and discharges (assists the pump force) during the outward stroke, and the shape of the cam track is designed to produce a desired operating profile for the pump.

20 Claims, 22 Drawing Sheets

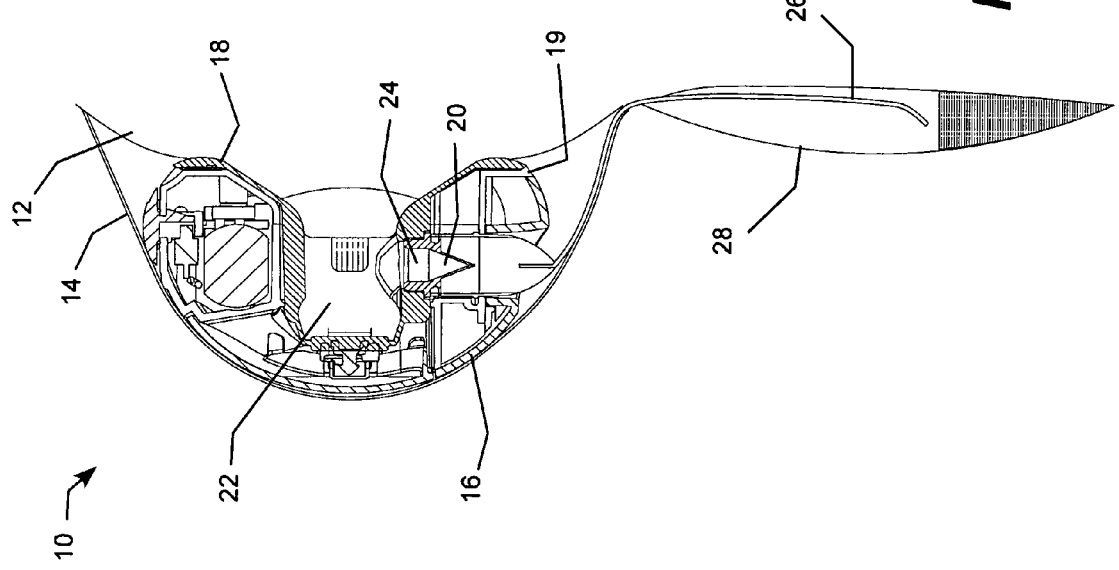

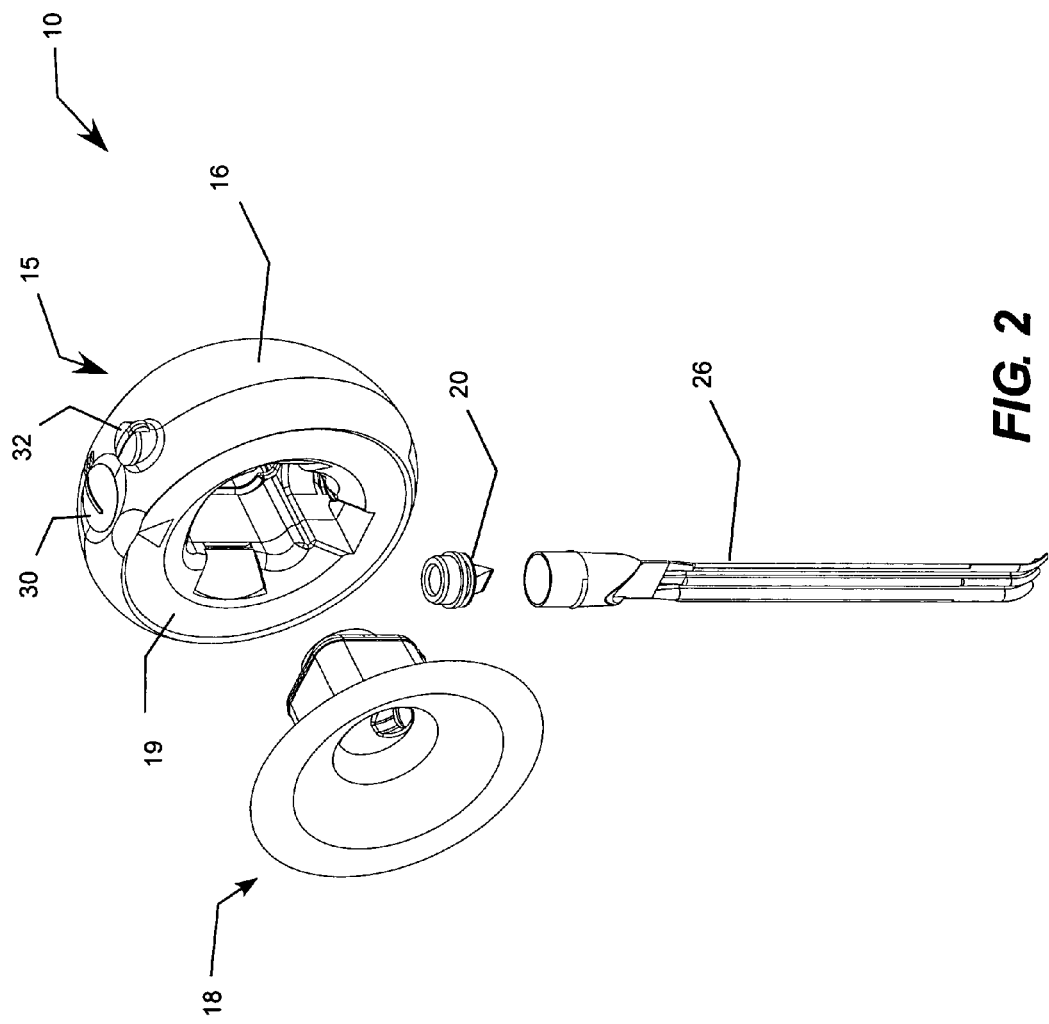

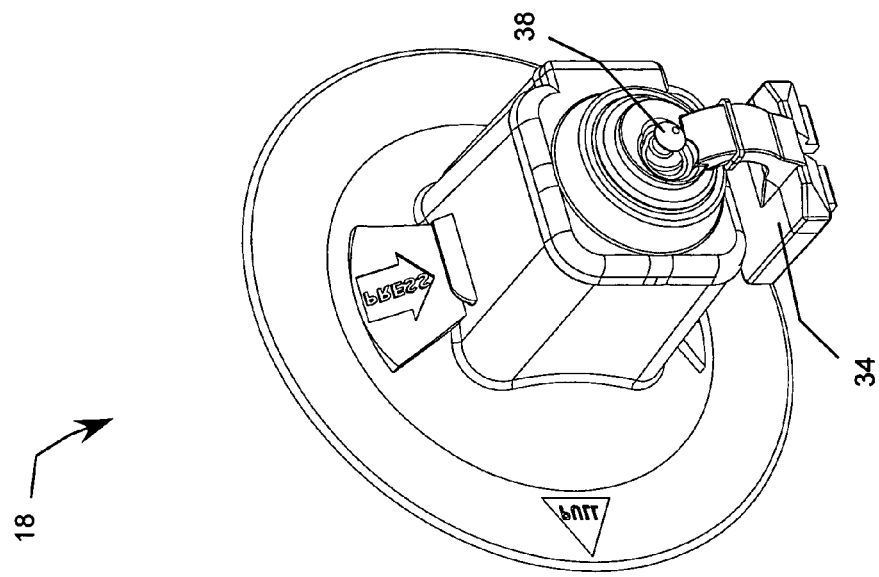
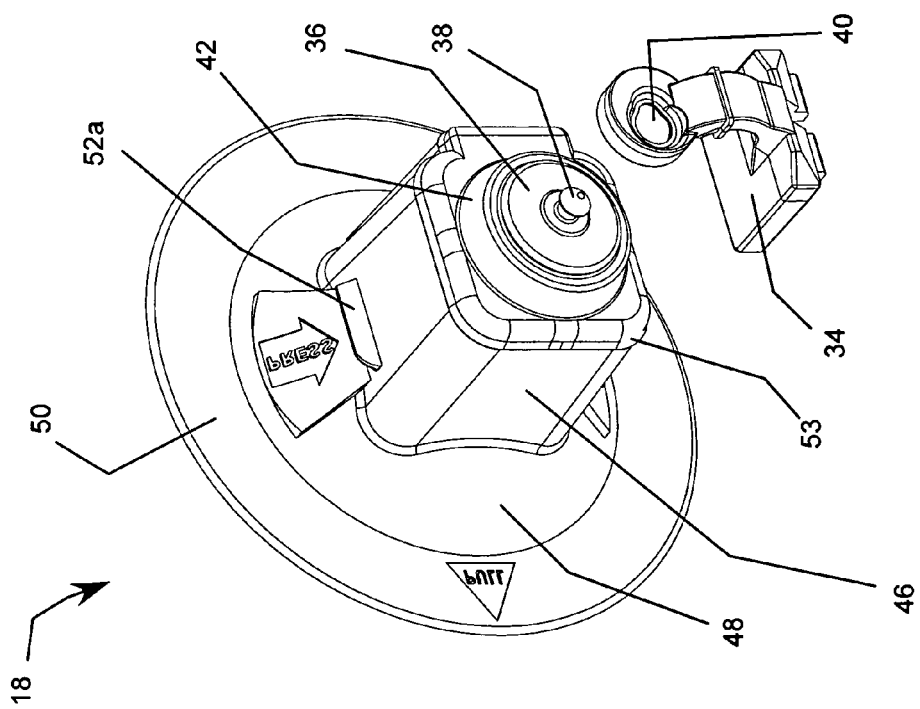

HANDS-FREE BREAST PUMP WITH BALANCED RECIPROCATING DRIVE

REFERENCE TO RELATED APPLICATION

This application claims priority to U.S. Provisional Patent Application Ser. No. 60/915,937 filed May 4, 2007 entitled "Hands-Free Breast Pump with Balanced Reciprocating Drive," which is incorporated herein by reference.

TECHNICAL FIELD

The present invention is generally related to breast pumps that cause nursing mothers to express breast milk and, more particularly, to a hands-free breast pump with a balanced push-pull vacuum generation system that applies pumping force to a bellows structure of a vacuum chamber formed by a breast interface cup during inward and outward pump strokes.

BACKGROUND OF THE INVENTION

The first hands-free breast pump including a self-contained pump mechanism and power source configured to be held in place between a nursing mother's breast and bra is described in U.S. Pat. No. 7,223,255 entitled "System For a Portable, Hands-Free Breast Pump and Method of Using the Same," which is incorporated herein by reference. The hands-free breast pump described in this patent, which will be referred to as the Gen-1 design, has been a successful commercial product. The present patent is directed to a second generation breast pump, which is referred to as the Gen-2 design, that includes significant improvements over the initial Gen-1 design.

More specifically, the Gen-1 design operates by applying force generated by a motor during the inward stroke of a pump mechanism to a movable part (referred to as a bellows structure) of a vacuum chamber located at the end of the breast cup (also referred to as breast interface flange). The force applied by the pump mechanism to the bellows structure of the vacuum chamber causes the bellows structure to partially collapse, thereby reducing the volume of the vacuum chamber to create positive pressure that forces any expelled milk located in the breast cup through a one-way valve and into a collection bag. Upon the release of the inward stroke of the pump mechanism, the bellows structure of the Gen-1 design is configured to resiliently recover its shape during an outward stroke to restore the original volume of the vacuum chamber, thereby increasing the volume of the vacuum chamber to create negative pressure within the vacuum chamber. The one-way valve vents the vacuum chamber during the inward stroke and seals the vacuum chamber during the outward stroke to create a milking action. That is, the outward stroke of the pump applies suction to the breast and the inward stroke forces the expressed milk through the one-way valve and into a collection bag.

As described above, the Gen-1 design utilizes an unbalanced pump mechanism that applies force to the vacuum chamber only during the inward stroke, whereas the resiliency of the bellows structure of the breast cup creates the suction during the outward stroke. Therefore, the pump mechanism is required to compress the bellows structure of the breast cup during the inward stroke, much like compression of a spring, sufficiently to allow the resiliency of the breast cup to generate the negative pressure that creates the suction action. Like a compressed spring, the bellows structure of the breast cup resiliently recovers its shape upon the release of the compression force to create the suction action without assistance from the pump motor, which applies force only during the inward stroke. While this type of pump mechanism is highly functional, it requires application of a significant force to the breast cup during the inward stroke, which tends to urge the breast cup out of its seat within the breast pump housing. Unless properly constrained, the force can be sufficient to cause the breast cup to pop out of its seat in the pump housing, which can cause the pump to malfunction. Although the breast cup can be restrained within its seat in the housing using a suitable device, such as tabs, detent mechanisms or a support ring, these features add complexity and cost to the pump.

Perhaps more importantly, the additional breast cup restraining features make the pump more difficult to assemble with the breast cup properly seated within the pump housing. Inevitably, a certain number of users are unable to assemble the pump correctly. Unfortunately, the pump looks and sounds like it is working properly even when the breast cup is not seated properly, and the user can find it difficult to detect that the breast cup is not seated properly. This gives some users who experience this problem the misimpression that the pump is assembled correctly and yet performs poorly, when the real problem is that the breast cup is not properly seated in the pump housing. Apparent pump malfunction due to improper breast cup seating has, therefore, been a recurring problem with the Gen-1 design.

The unbalanced nature of the Gen-1 pump design (i.e., the application of motor force only during the inward stroke) also requires a relatively powerful pump motor to compress the bellows structure of the breast cup on the inward stroke against an amount of natural resiliency of the silicon that is sufficient to generate the desired suction within the breast cup on the outward stroke. Pumping against this amount of spring force on the inward stoke, without the assistance of the motor on the outward stroke, is inefficient because the motor is used in an unbalanced manner in that high force is applied from the motor on the inward stroke, whereas no force is applied by the motor on the outward stroke. This unbalanced pump design requires higher power, reduces the cycle rate, taxes the motor, and stresses the internal gear train components to a higher degree than could be obtained from a more balanced design. Accordingly, there remains a need for more effective, efficient and user friendly hands-free breast pump designs.

SUMMARY OF THE INVENTION

The present invention meets the needs described above in a second generation hands-free breast pump, referred to as the Gen-2 design, that includes a balanced push-pull vacuum generation system that applies pumping force to a bellows structure of a vacuum chamber formed by a breast interface cup during the inward and outward pump strokes. More specifically, the breast pump includes a breast cup that has a resilient bellows structure that partially collapses the volume of the vacuum chamber during the inward stroke and recovers the volume of the vacuum chamber during the outward stroke. The pump mechanism, which includes a cam drive system that translates rotary electric motor power into reciprocating linear action of an actuator arm that drives the bellows structure, applies force to the bellows structure during the inward pump stroke causing a reduction in the volume of the vacuum chamber and during the outward pump stroke causing an expansion of the volume of the vacuum chamber. The bellows structure acts like a spring that charges (resists the pump force) during the inward stroke and discharges (assists the pump force) during the outward stroke, and the shape of the cam track is designed to produce a desired operating profile for the pump. In addition, the shape of the cam track is carefully designed and fine tuned to produce a desired operating profile for the pump to mitigate motor current spikes, undue gear stress and reduce noise while producing a desired suck-release profile for the pump.

The use of a balanced drive system that applies force to the bellows structure of the breast cup during both the inward and outward pump strokes reduces the resiliency required of the bellows structure of the breast cup from that of the Gen-1 design, resulting in a more effective, efficient and user friendly hands-free breast pump design. For example, the Gen-2 pump running on a single AA battery achieves comparable suction levels at a comparable cycle rate when compared to the Gen-1 design running on two AA batteries. In addition, the reduced pumping force of the Gen-2 design allows this embodiment to achieve improved performance with a motor operating at significantly lower RMP and a significantly smaller gear ratio, which reduces the required number of gear meshes and allows for larger, more robust gears. These design improvements result in a lower cost, better performing, quieter and more robust breast pump that is easier to manufacture, easier to assemble, and has significantly fewer parts in the pump drive train. The Gen-2 pump also incorporates a number of other important design improvements, as described in more detail below. These additional features and advantages of the Gen-2 pump will become apparent to the skilled artisan upon examination of the following drawings and detailed description. It is intended that all such additional features and advantages be included within the scope of the present invention.

BRIEF DESCRIPTION OF THE DRAWINGS

FIG. 1 is a cross sectional side view of a hand-free breast pump held in its operative position between the breast of a nursing woman and the cup of a bra worn by the woman while the pump is actively pumping breast milk into a collection bag supported by the breast pump and bra.

FIG. 2 is a an exploded perspective view showing the major components of the hand-free breast pump and accessories including the breast pump, the breast cup, the one-way valve, and the milk transport stem.

FIG. 5 is a perspective view of a breast cup for a hands-free breast pump prior to engagement with the actuator arm of the breast pump.

FIG. 6 is a perspective view of the breast cup of FIG. 5 after engagement with the actuator arm of the breast pump.

DETAILED DESCRIPTION OF THE EXEMPLARY EMBODIMENTS

Figure 4:
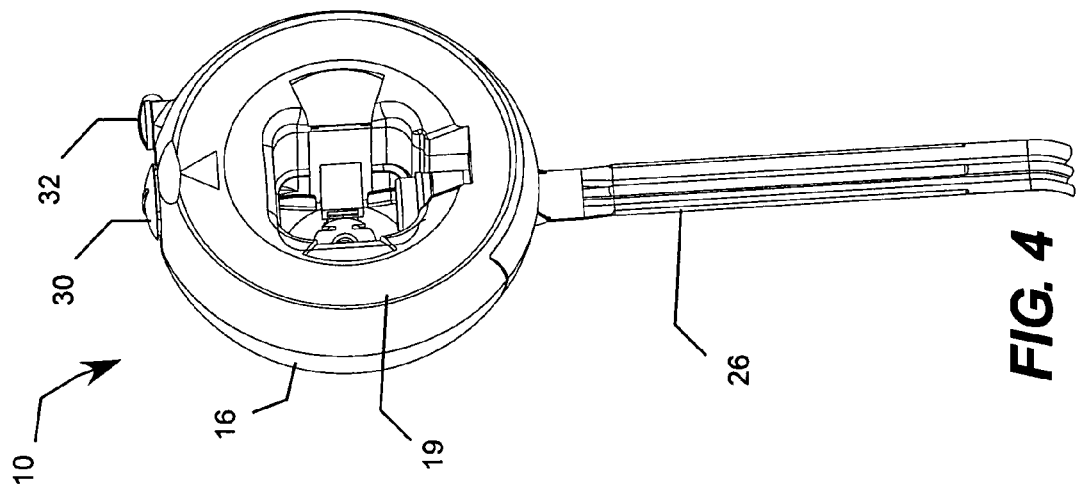
FIG. 4 is a perspective view of an assembled hands-free breast pump of FIG. 3 with the breast cup removed.

The present invention may be embodied in a hands-free breast pump with a balanced push-pull mechanical actuator and cam drive system that applies pumping force to a bellows structure of a breast interface cup during inward and outward pump strokes. As the Gen-1 design applied no motor force to the bellows structure on the outward pump stroke, configuring the Gen-2 pump to apply any amount of motor force to the bellows structure during both the inward (push) and outward (pull) strokes achieves some level of balance in the drive system and therefore improves the balance over the Gen-1 design. Significant attention has been paid to this design feature in the Gen-2 pump, which achieves a relatively high level of balance, for example where the force applied by the pump during the inward stroke is within eighty percent (80%) of the force applied during the outward stroke. In the particular embodiment shown in the figures and described below, the Gen-2 pump is well optimized to achieve even higher levels of balance, for example where the force applied by the pump during the inward stroke is within ninety percent (90%) or more of the force applied during the outward stroke during the normal operating mode. This high level of balance is achieved through careful design of the resilient bellows structure of the breast cup and the cam drive system of the breast pump that translates rotary electric motor power into reciprocating linear action of the actuator arm to efficiently develop a desired pump operating profile. The bellows structure acts like a spring that charges (resists the pump force) during the inward stroke and discharges (assists the pump force) during the outward stroke, and the shape of the cam track is carefully designed and fine tuned to produce a desired operating profile for the pump.

In the Gen-2 breast pump, the primary components of the milk collection system include a silicone breast cup with a collapsible bellows structure at the end of the nipple tunnel (also called the vacuum chamber) which serves to displace air and produce a vacuum within the breast cup. The vacuum chamber is vented by a silicone one-way valve that opens during the inward (positive pressure) pump stroke to allow air and milk to be exhausted from the nipple tunnel, and then closes during the outward (negative pressure) pump stroke to seal the nipple tunnel and allow vacuum to be created within the nipple tunnel. The milk expressed from the breast is expelled from the breast cup through the one-way valve, along a wave-shaped splint or open straw (also called a stem), and into a freezer grade, polyethylene or similar milk collection bag. The breast pump is held between the user's breast and the cup of her bra (also called a brassier), the stem and neck of the collection bag pass between the user's chest and the bottom edge of the bra, and the retention area (pouch portion) of the collection bag is supported below the bra. The flexible, wave-shaped splint or open straw that inserts into the neck of the milk collection bag allows a simple snap connection to the breast pump housing, while also serving as a splint to keep an open path in the neck of the milk collection bag for the milk to travel under the taut band of the user's bra and into the retention area of the milk collection bag.

The Gen-2 pump mechanism includes a rotary electric motor that moves an actuator arm through a reciprocating linear motion. The actuator arm interfaces with a barb connected to a disc, which is connected to the flange top at the end of the nipple tunnel of the breast cup. The nipple tunnel forms a vacuum chamber when the breast cup forms an air-tight seal with the user's breast. The linear reciprocating motion of the actuator arm moves a bellows structure at or near the end of the nipple tunnel reciprocally through an inward stroke and an outward stroke. The inward stroke partially collapses the volume of the vacuum chamber and the outward stroke restores the volume in a repeating cycle to alternately create and release suction within the nipple tunnel.

The Gen-2 pump includes a self-contained pump unit and power source enclosed within a dome shaped housing that receives and supports the removable breast cup. The housing compactly contains the pump motor, the drive train, and a power source, such as one or more batteries, and the associated electrical and mechanical features of the pump. In the embodiment described in detail below, for example, the pump achieves acceptable performance using a single AA battery as the power source. The pump housing with a received breast cup fits discreetly between the user's breast and a breast cup of a normal brassiere. It should also be appreciated that the motorized drive train could be replaced by a manually operated drive mechanism. In addition, the battery could be replaced by a connector to an external power source, such as an electrical plug connected to a DC power source (such as an automotive power supply) or an AC power converter configured to plug into a conventional AC power outlet.

Balanced operation of the motor and drive train, which results in motor force applied to the vacuum chamber during the inward and the outward strokes during the normal use mode, represents a key improvement of the Gen-2 design over the Gen-1 design. In fact, the Gen-2 pump achieves a high level of balance in the motor and drive train operation, resulting in a substantially similar amount of motor force applied to the vacuum chamber during the inward and the outward strokes. This highly balanced motor and drive train operation reduces the maximum force required from the motor and drive train, which allows the Gen-2 pump to use a lower-RPM motor and a lower gear ratio while achieving higher pump cycling rates, lower power consumption, and longer battery life.

Another Gen-2 improvement is found in the design of the bellows structure that creates the suction within the breast cup. The Gen-2 bellows structure has a substantially reduced surface area translating at the end of nipple tunnel, presenting reduced resistance to the inward stroke and a more efficient movement of the resilient silicon. The reduced resistance of the bellows structure, which allows for the reduction in pump force applied to the bellows structure, also improves the vacuum retention of the breast cup by significantly reducing vacuum lost due to collapse and flexure of the nipple tunnel portion of the breast cup area near the bellows structure. The breast interface portion of the breast cup has also been improved to include an extended funnel-shaped section, which extends further up the breast surface to contact a larger portion of the breast to more evenly distribute the pressure between the breast cup and the breast. This avoids pressure points on the breast that could otherwise result from tight or unevenly fitting brassieres that tend to press the breast pump firmly against the breast. The improved pressure distribution allows less compression of milk ducts, thereby improving milk flow from the breast and into the pump.

The Gen-2 breast cup includes additional improvements, including side walls of the nipple tunnel that are sufficiently thick to be rigid enough to retain its shape (i.e., avoid partial collapse of the nipple tunnel and resulting vacuum loss) under the highest vacuum applied by the pump mechanism without a supplemental rigid support ring. The breast cup retention features, including the retention rib and detent mechanisms retaining the breast cup within the pump housing, have been relocated to be proximate to the bellows structure at the extreme rear of breast cup (i.e., near the flange top or end of the nipple tunnel) to counter the pump force applied during the inward stroke that tends to urge the breast cup out of its seat in the housing. Locating the breast cup support features adjacent to the bellows structure also helps to provides shape retention assistance in that area of the breast cup.

The barb shaped breast cup retention rib on the rear flange perimeter also allows easy insertion by the user while offering good retention in the housing while in use. Side barbs on the outer walls of the nipple tunnel function as detent mechanisms that provide tactile and audible feedback letting user know when breast cup has been fully inserted into the pump housing. The rounded shape of the ends of these barbs facilitates removal of the breast cup from the housing and prolongs the life of the breast cup. Recessed seating of the one-way valve provides a helpful visual cue to the user when the valve is fully seated and aids in valve retention in the breast cup when the cup is inserted and removed from housing.

On the interior of the nipple tunnel, the length of the vacuum chamber has been increased to reduce the chance of end of the user's nipple "bottoming out" or contacting the flange top at the end of the nipple tunnel attached to the movable bellows structure during the inward pump stroke. The thick and rigid side walls of the nipple tunnel prevent the tunnel from collapsing and pinching the user's nipple under the vacuum created during the outward stroke. The bottom surface of the nipple tunnel on the interior of the nipple tunnel is angled downward toward the outlet to prevent milk from pooling in the end of the nipple tunnel, which could otherwise lead to spills or waste. The bottom surface of the nipple tunnel also includes a distinct trough or milk flow channel leading to a larger, more funnel shaped outlet in the bottom of the nipple tunnel to aid in effective flow of milk out of the nipple tunnel area and into the outlet for efficient transport into the milk collection bag. In addition, a lofted "dam" of material is located between the outlet and the front of the nipple tunnel where the breast cup interfaces with the user's breast to minimize the chance that milk could flow back out of the nipple tunnel and onto the user's clothing.

The push-pull vacuum generation action of the Gen-2 design actively creates consistent vacuum levels by forcing a repeatable level of nipple tunnel volume expansion and contraction. The barb at the end of the nipple tunnel, which allows the actuator arm to both push and pull on the flange top, is shaped to facilitate both engagement with, and disengagement from, the detent opening in the actuator arm without special user intervention. The breast cup mold includes slots that allow sufficient silicon to flow into the disc retention area of the breast cup to create a strong connecting layer of material holding the disc in place to produce a durable breast cup. The one-way valve has a larger opening that allows milk to flow more freely and evacuate the nipple tunnel of the breast cup more efficiently.

In the Gen-2 pump, an electro-mechanical movement replaces the electronically controlled drive of the Gen-1 design, yet still allows for adjustment of both vacuum level and cycle rate. The cam drive system of the Gen-2 pump reduces the complexity and cost of the pump. In addition, the cam drive system allows the reciprocating, push-pull linear action of the actuator arm with a force distribution curve that can be controlled by carefully designing the shape of the cam track to maximize efficiency and reduce gear and motor stress. The net benefit is a higher pump cycling rate with a lower speed, quieter motor. The smaller gear ratio allows the Gen-2 pump to utilize a smaller number of larger, more robust and quieter gears. The reduction in total gear ratio requirement provided by the Gen-2 cam drive system allows for larger gears with more tooth surface contact. In addition to higher strength and reliability, these larger toothed gears can be fabricated in softer materials which, combined with the additional surface contact and lower operating speed, serves to significantly quiet the drive train operation.

The Gen-2 pump also includes an interference-based vacuum adjustment mechanism. Specifically, two parallel, partially co-planar sliding panels (i.e., the cam follower and the actuator arm) are joined by a coil spring that is preloaded to effectively lock the two panels together during normal, maximum vacuum operation. However, when the linear motion of the actuator arm panel is impeded by the shaft of the vacuum adjust mechanism, the actuator arm panel no longer translates inward with the movement of the cam follower panel. Instead, the cam follower panel continues to move according to its relationship with the cam path of the cam gear. The difference in translation of the two panels is absorbed by the compression of the spring linkage of the two panels. Under expected normal use, the user will operate the pump at full vacuum and no interference by the vacuum adjustment mechanism, and therefore no additional, forced compression of the linking spring. Thus, the normal use is the most efficient operating mode. The spring linkage between the cam follower and the actuator arm also produces the benefit of allowing the motor and gear train to continue to cycle without becoming jammed in the event that the motion of the actuator arm is impeded, for example when the actuator arm is blocked by an external object or manually held in place.

Turning now to the figures, in which like element numerals refer to like elements throughout the several figures, a particular embodiment of the Gen-2 breast pump is shown in the figures and described in the accompanying text. The Gen-2 breast pump leverages the successful technology from the original Gen-1 pump design and significantly improves upon performance, ease of use, manufacturability and reliability. The intended use of the Gen-2 pump as supported between the user's breast and the cup of a normal brassier and the overall approach to milk collection remains largely unchanged from the Gen-1 design, whereas the Gen-2 pump mechanism and breast cup have been substantially redesigned to achieve a number of major improvements.

FIG. 1 is a cross sectional side view of a hand-free Gen-2 breast pump 10 held in its operative position between the breast 12 of a nursing woman and the cup 14 of a brassier worn by the woman while the pump is actively pumping breast milk from the woman's breast. The breast pump 10 includes a dome-shaped outer housing 16 that faces the inner surface of the brassier cup 14 and an inner housing 19 that receives the breast cup 18, which interfaces with the woman's breast 12. The breast cup 18 includes a nipple tunnel that forms a vacuum chamber 22 between the breast cup and the woman's breast, which is vented through an opening or outlet 24 through the bottom of the breast cup. The outer housing 16 can include a transparent window (e.g., the removable cover plate 65 shown in FIG. 23) to allow the user to see the position and condition of the nipple after the breast pump has been placed in its operative position against the breast. This allows the user to adjust the position of the pump against the breast to center the nipple in the nipple tunnel, and also allows the user to observe the nipple during pumping, which can be helpful, for example, to maintain awareness of milk letdown, milk flow and nipple inversion.

Figure 12:
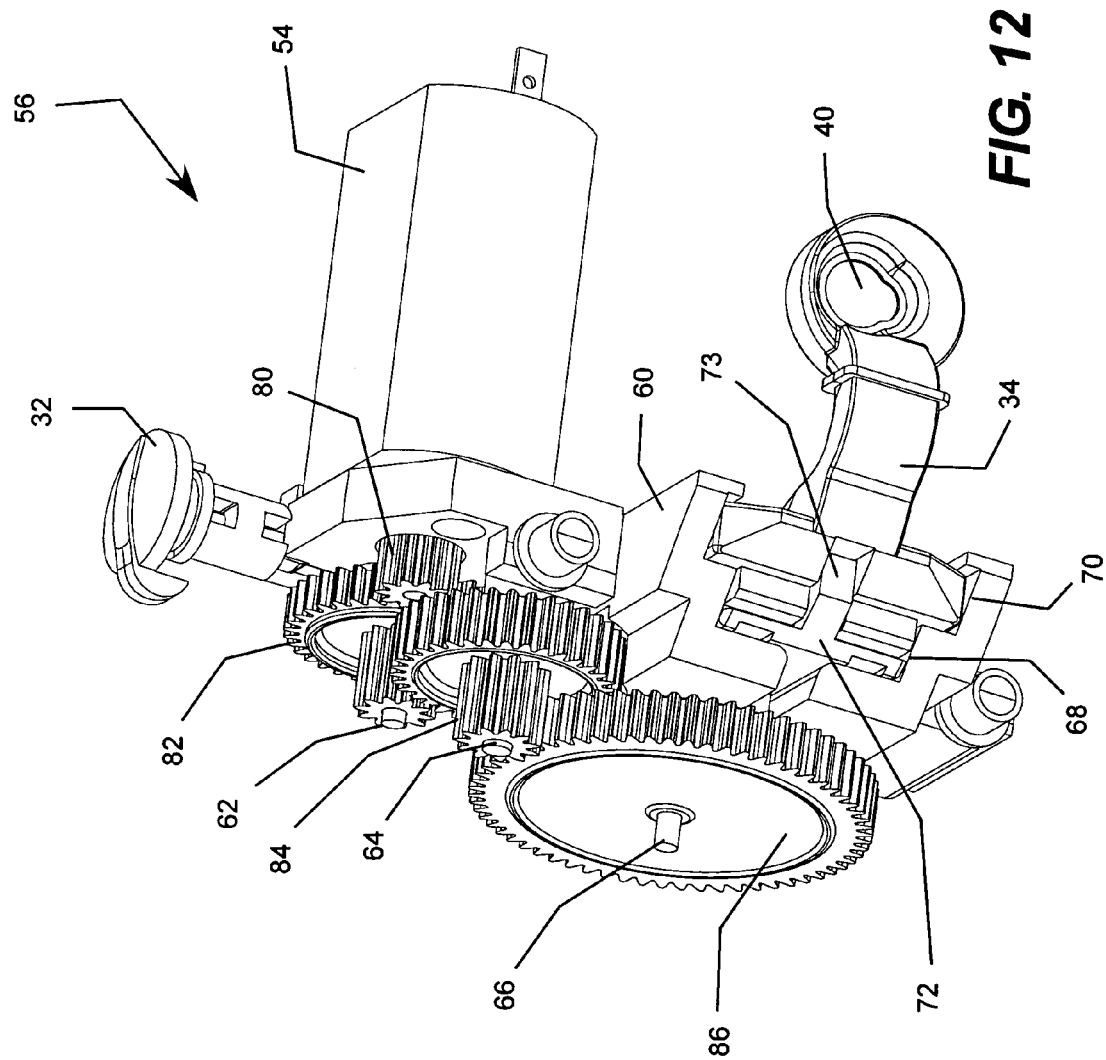
FIG. 12 is an assembled perspective view of the drive train of the breast pump.
Figure 13:
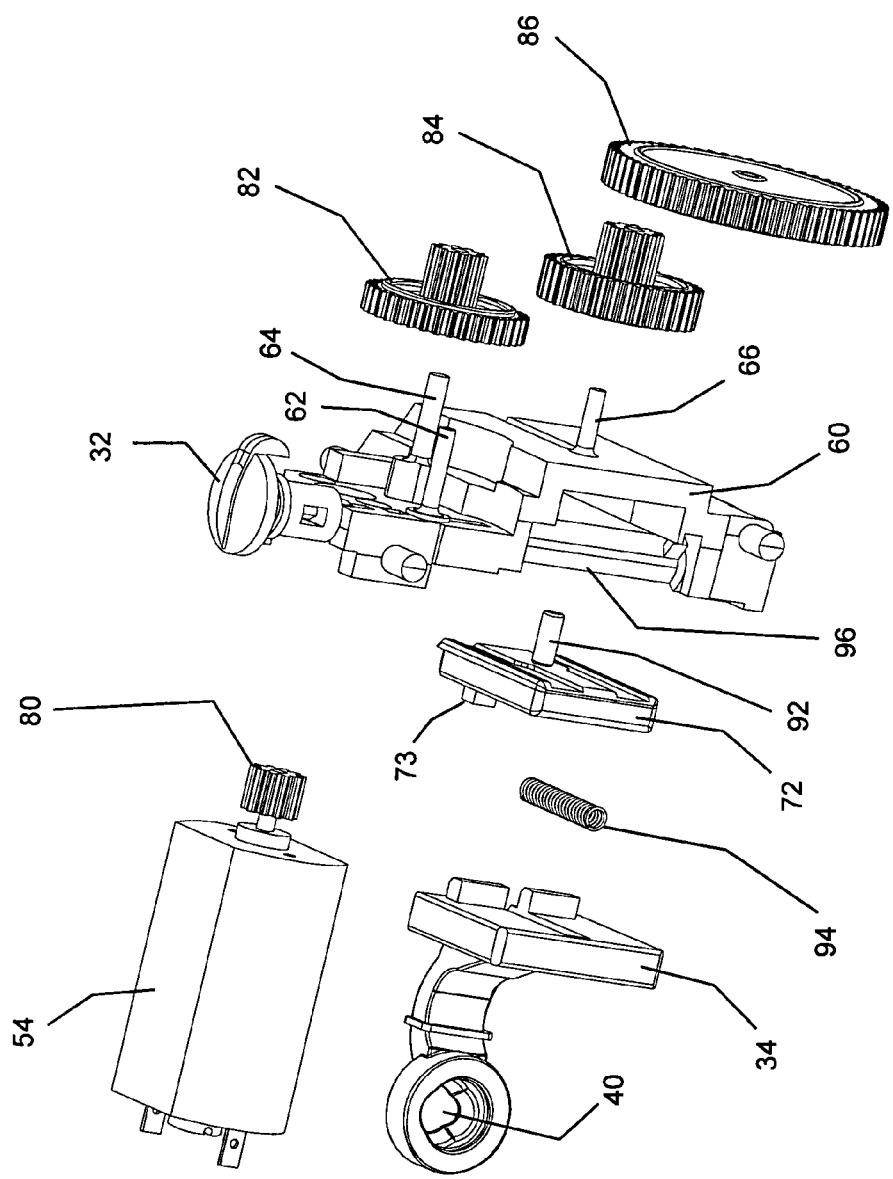
FIG. 13 is a first exploded perspective view of the drive train of the breast pump.
Figure 14:
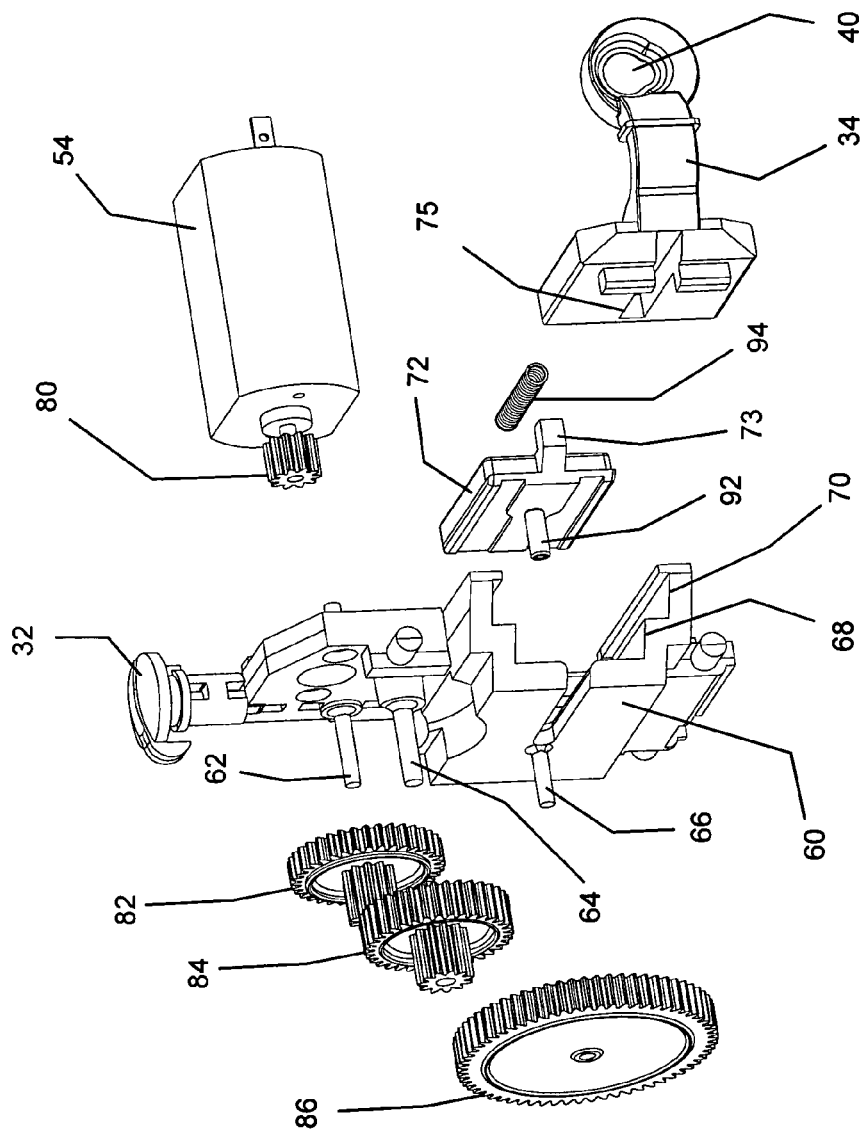
FIG. 14 is a second exploded perspective view of the drive train of the breast pump.

During its inward stroke, the pump mechanism (shown best in FIGS. 12-14) pushes on an integrated (molded-in) disk located at the end of the vacuum chamber (also called the flange top) to cause a bellows structure (shown best in FIGS. 9A-B, 17 and 18) located at or near the end of the vacuum chamber to partially collapse (move inward) and thereby reduce the volume of the vacuum chamber to create positive pressure within the vacuum chamber. During its outward stroke, the pump mechanism pulls on the barb attached to the disk at the top of the vacuum chamber causing the bellows structure to recover its original shape (move outward) to restore the original volume of the vacuum chamber, thereby increasing the volume of the vacuum chamber to create negative pressure within the vacuum chamber. A one-way valve 20 vents the vacuum chamber during the inward stroke and seals the vacuum chamber during the outward stroke to create a milking action. The expressed milk is forced through the outlet 24, through the one-way valve 20, along the exterior surface of the wave-shaped stem 26, and into a collection bag 28 that is supported by the breast pump and the elastic, wire or other structure at the bottom edge of the brassier.

FIG. 2 is an exploded perspective view showing the major components of the hand-free breast pump 10 including the pump enclosure 15 that contains the pump mechanism and power source, the breast cup 18, the one-way valve 20 and the stem 26. The pump enclosure 15 includes a dome-shaped outer housing 16 and an inner housing 19 configured to receive the breast cup 18. The breast pump 10 also includes a sliding power control switch 30 and a vacuum control knob 32. In this particular embodiment, the power control switch 30, which affects the cycling rate of the pump, includes three settings, fast, slow and off. The vacuum control knob 32 may be turned through a rotation range that is slightly less than a full rotation to adjust the vacuum level by adjusting the pump stroke length.

Figure 3:
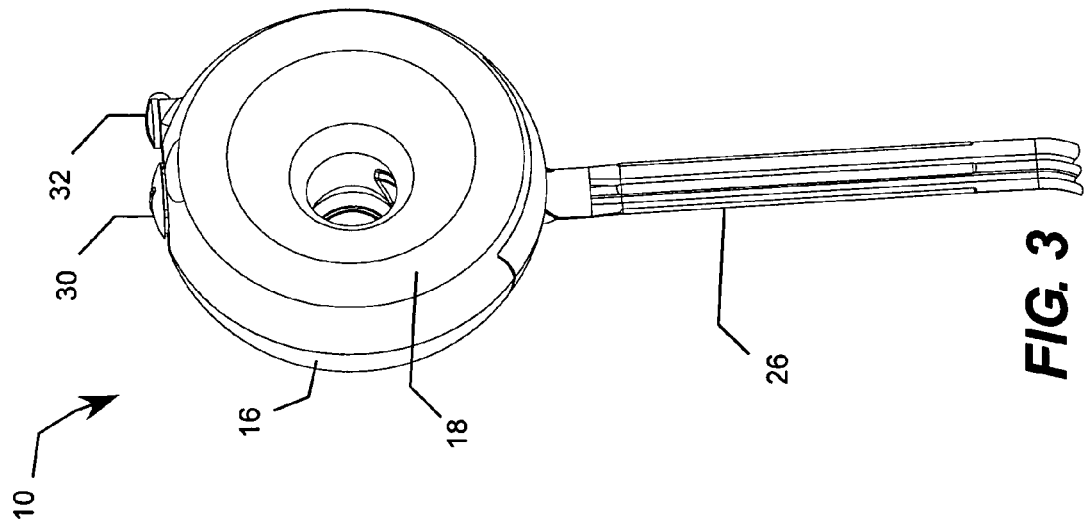
FIG. 3 is a perspective view of an assembled hands-free breast pump with the breast cup installed in its operative position.

FIG. 3 is a perspective view of an assembled hands-free breast pump 10 with the breast cup 18 installed in its operative position. FIG. 4 is a perspective view of the breast pump with the breast cup removed. These views also show the power switch control knob 30 and the vacuum control knob 32. Although this embodiment includes a three-position power switch, the cycle rate adjustment mechanism may include a larger number of available rate settings, such as a slider, dial or multi-position selection switch that allows the user to control the cycle rate of the pump. Cycle rate adjustment is typically accomplished by adjusting the voltage applied to the pump motor, for example through a resistive voltage divider or voltage-limiting diodes. The vacuum adjustment knob 32 allows the user to adjust the strength of the vacuum or suction generated by the pump. Vacuum adjustment is typically accomplished by adjusting the stroke length of the pump actuator arm, in this embodiment through an eccentric cam surface on a shaft connected to the vacuum adjustment knob 32. The eccentric cam of the vacuum adjustment mechanism selectively blocks and thereby adjusts the stroke length of the pump actuator arm.

FIG. 5 is a perspective view of the breast cup 18 prior to engagement with the actuator arm 34 of the breast pump. The breast cup 18 includes a flange top 36 at the end of a nipple tunnel 46 that includes an over-molded disk having an attached barb 38 that engages with a keyhole or teardrop shaped detent opening 40 in the actuator arm 34. FIG. 6 shows the breast cup 18 with the barb 38 engaged in the detent opening 40. The barb 38 and detent opening 40 are configured such that the barb securely engages with the detent opening when the breast cup is received within the breast pump, and the barb releases from the detent opening when the beast cup is removed from the breast pump. The breast cup 18 also includes a bellows structure 42, which is shown in FIG. 5 in its outward position. The bellows structure 42 is also shown in the outward position in FIGS. 6, 8, 9A, 16, 17 and 19. During the inward stroke of the pump mechanism, the actuator arm 34 pushes the flange top 36 to its inward position, which causes the bellows structure 42 to reduce the volume of the vacuum chamber formed by the nipple tunnel and thereby create positive pressure within the vacuum chamber. The bellows structure 42 is shown in the inward position in FIGS. 9B, 18 and 20. During the outward stroke, the actuator arm 34 pulls the flange top 36 back into its outward position, which causes the bellows structure to increase the volume of the vacuum chamber and thereby create negative pressure or suction within the vacuum chamber. The resiliency of the bellows structure 42 resists the inward stroke and assists in the outward stroke, aiding in the balanced operation of the pump. In normal use mode, with the breast cup producing vacuum, the outward force of the natural resiliency of the bellows structure largely offsets the inward force of vacuum created within the breast cup, resulting in balance in the pump operation.

The vacuum chamber of the breast cup 18 is formed by the nipple tunnel 46 having side walls that are sufficiently thick to prevent the side walls from collapsing from the high vacuum generated during the reciprocal action of the bellows structure 42. That is, the nipple tunnel 46 is sufficiently rigid to support the reciprocal action of the bellows structure 42 without further support from a support ring or other structure within the pump housing. This is a significant improvement over the Gen-1 breast cup design, which requires a separate support ring for additional support.

Figure 15:
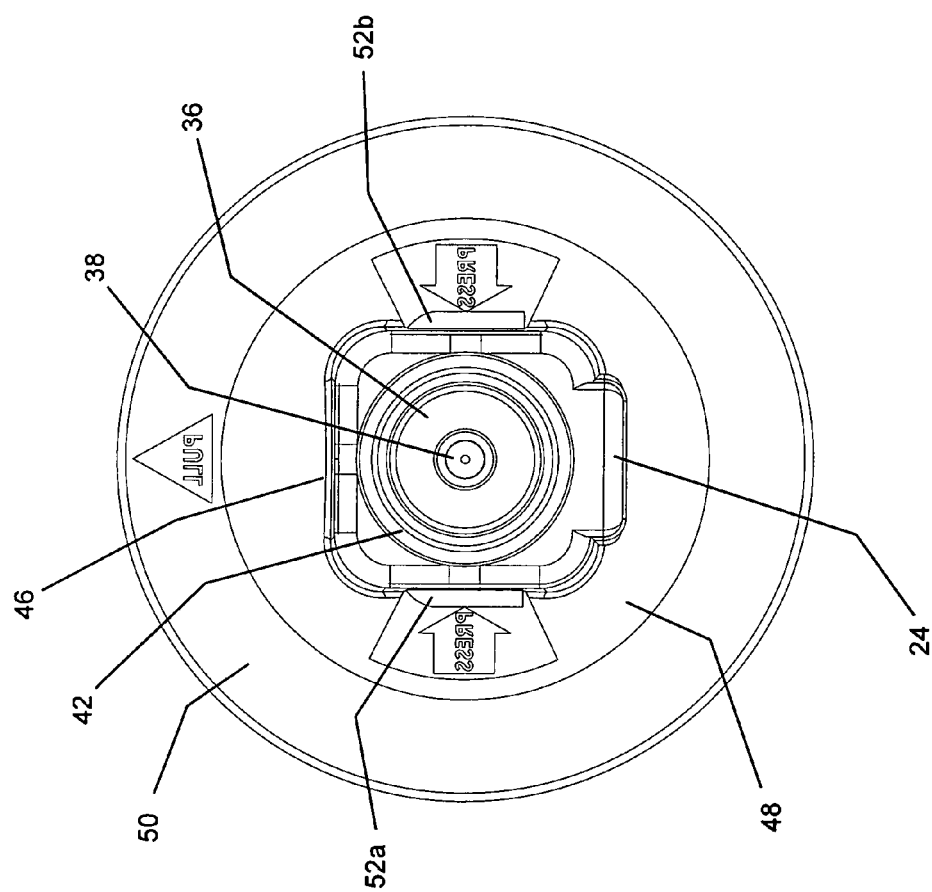
FIG. 15 is an end view of the breast cup.
Figure 16:
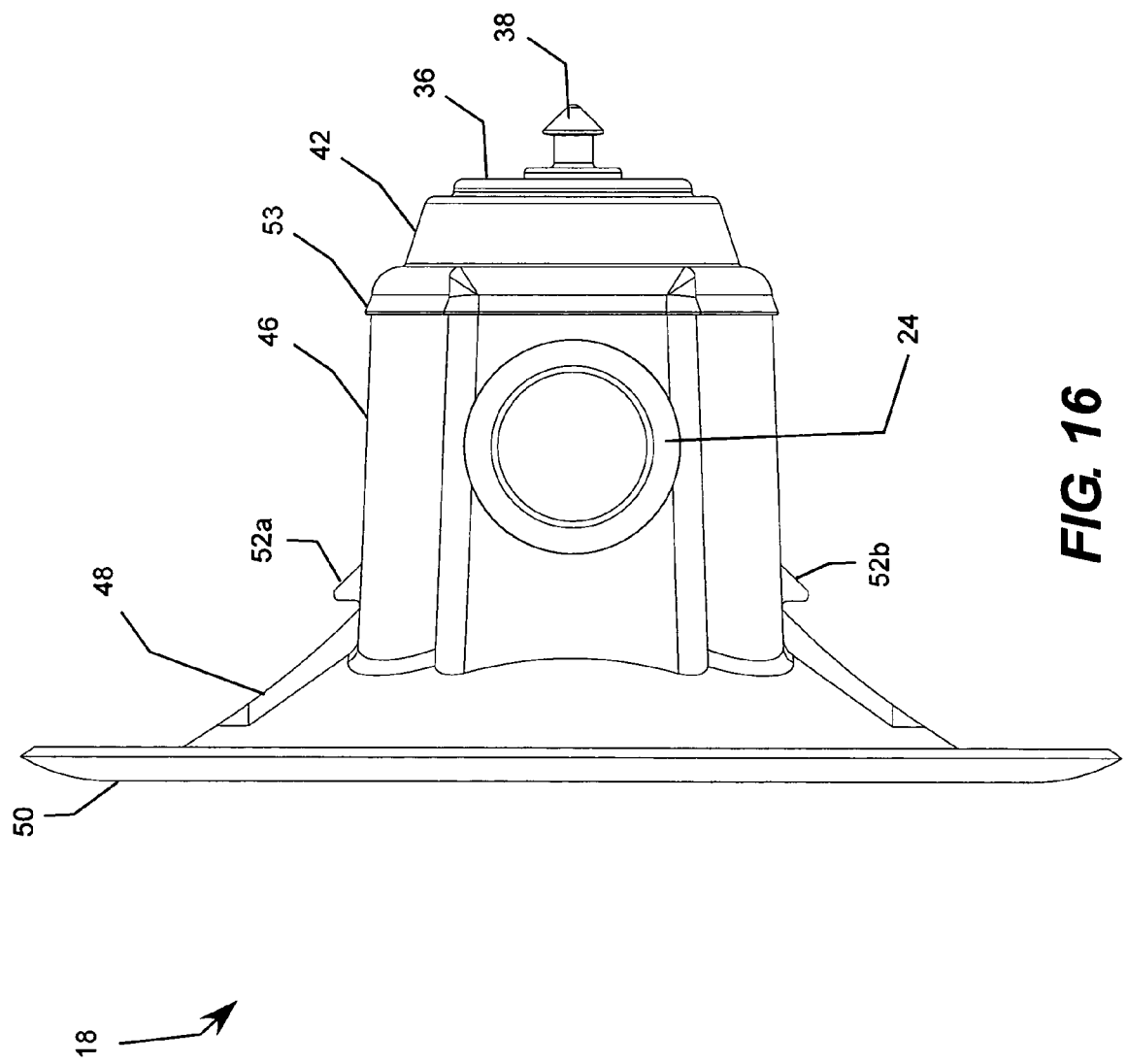
FIG. 16 is a bottom view of the breast cup.

The breast cup 18 also includes a funnel shaped breast interface section 48, which spreads the breast contact surface and the associated compressive force (pressure) over a significantly larger portion of the breast and breast cup. The breast cup also includes an outer flange area 50, that together with the interface section, form an air-tight seal with the woman's breast. Spreading out the breast contact surface area reduces the possibility of undesired restriction of milk flow due to compression of milk ducts in the breast. The breast cup 18 is held within the pump housing with a catch rib 53 located toward the end of the exterior wall of the nipple tunnel proximate to the bellows structure 42. A pair of detent tabs located on the exterior wall of the nipple tunnel "click into place" to provide the user with tangible, audible feedback indicating that the breast cup is fully inserted into the housing. One detent tab 52a is shown in FIG. 5 and an opposing detent tab is located on the opposite side of the nipple tunnel 46. Both detent tabs 52a and 52b are shown in FIGS. 15 and 16.

Figure 8:
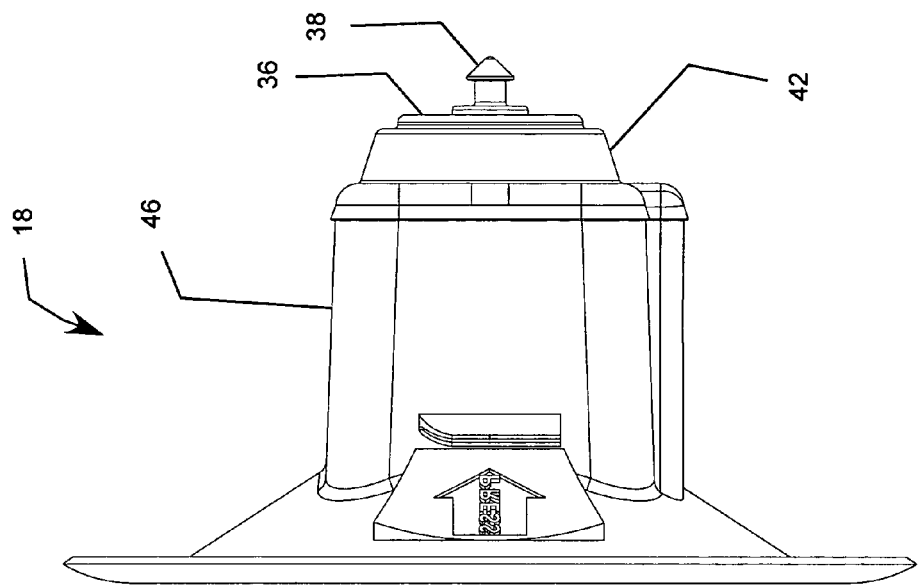
FIG. 8 is a side view of the breast cup.
Figure 7:
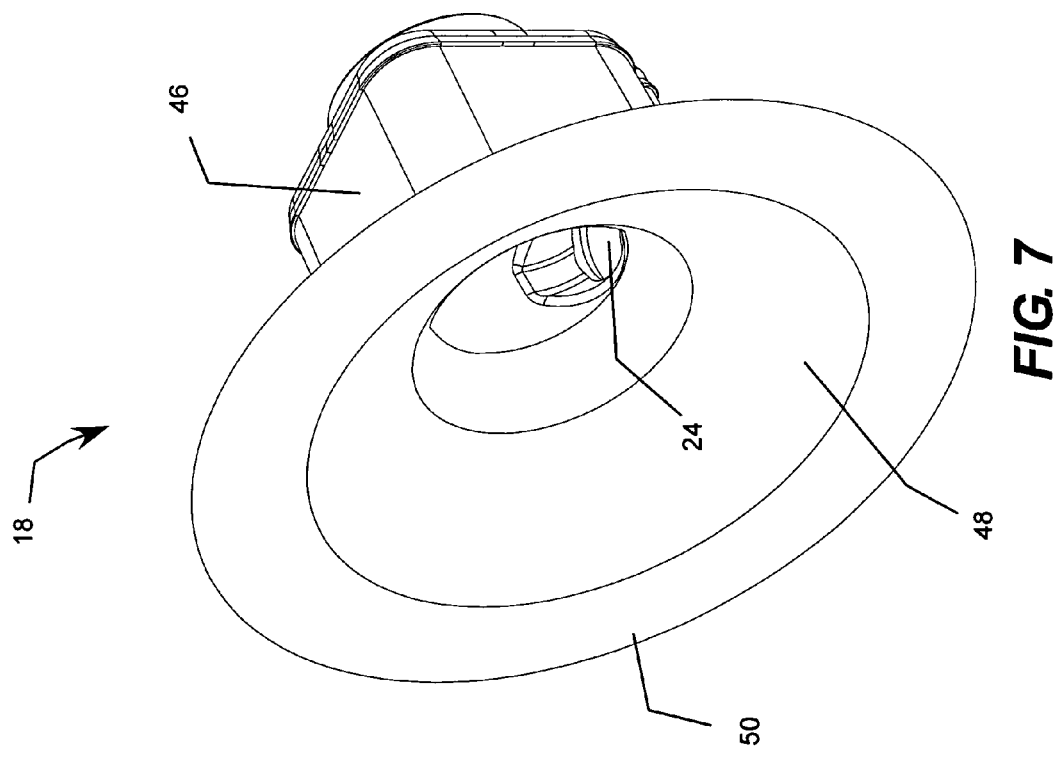
FIG. 7 is a perspective view of the breast cup showing the opening for receiving the one-way valve.
Figure 9B:
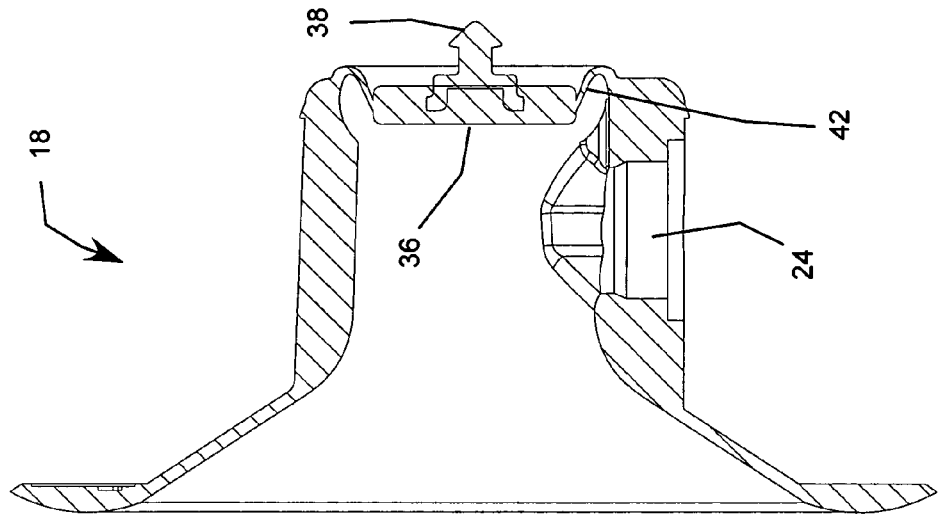
FIG. 9B is a cut-away side view of the breast cup showing the flange top in the inward position.
Figure 9A:
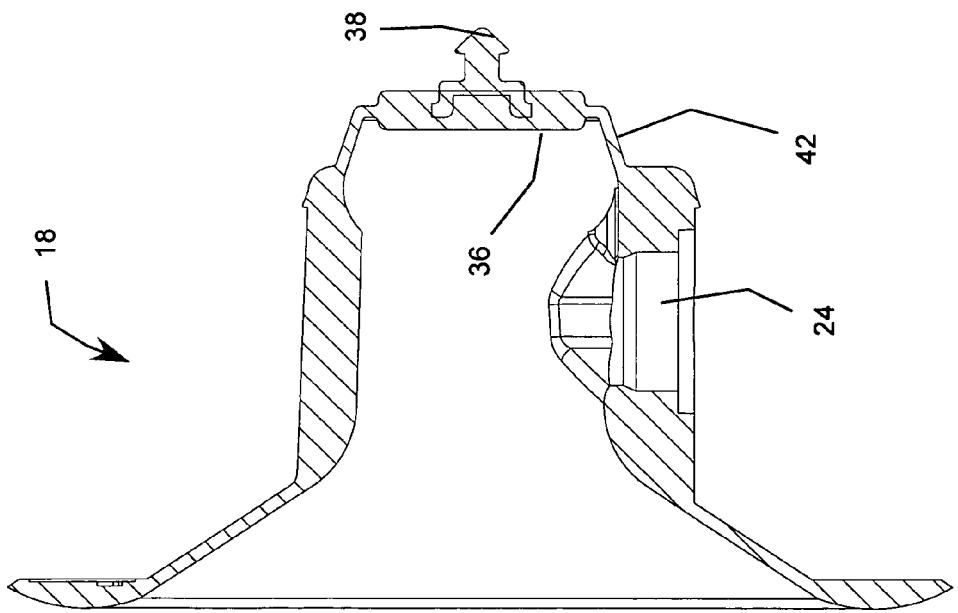
FIG. 9A is a cut-away side view of the breast cup showing the flange top in the outward position.

FIG. 7 is a perspective view of the breast cup 18 showing the nipple tunnel 46, breast interface section 48, outer flange area 50, and the outlet 24 that receives the one-way valve. FIG. 8 is a side view of the breast cup 18. FIG. 9A is a cut-away side view of the breast cup 18 showing the flange top 36 in the outward position. FIG. 9B is a similar view showing the breast cup 18 with the flange top 36 in the inward position. During the inward pump stroke, the actuator arm of the breast pump pushes the flange top 36 from the outward position shown in FIG. 9A to the inward position shown in FIG. 9B, which creates positive pressure inside the vacuum chamber formed by the breast cup and the user's breast. During the inward stroke, the one-way valve located in the outlet 24 vents the positive pressure, which expels milk from the breast cup through the outlet. During the outward pump stroke, the actuator arm of the breast pump pulls the flange top 36 from the inward position shown in FIG. 9B to the outward position shown in FIG. 9A, which creates negative pressure (suction) inside the vacuum chamber. During the outward stroke, the one-way valve located in the outlet 24 seals the outlet, which causes the negative pressure (suction) to be sustained within the vacuum chamber to create a milking action promoting the expression of milk from the user's breast. As noted previously, the bellows structure 42 resiliently resists the inward stroke and assists the outward stroke such that, when the breast cup is operating in its normal mode cyclically creating and sustaining suction during the outward stroke and expelling milk through the outlet vented by the one-way valve during the inward stroke, the amount of force applied by the pump mechanism to the flange top 36 is substantially the same during the inward and outward pump strokes.

Figure 10:
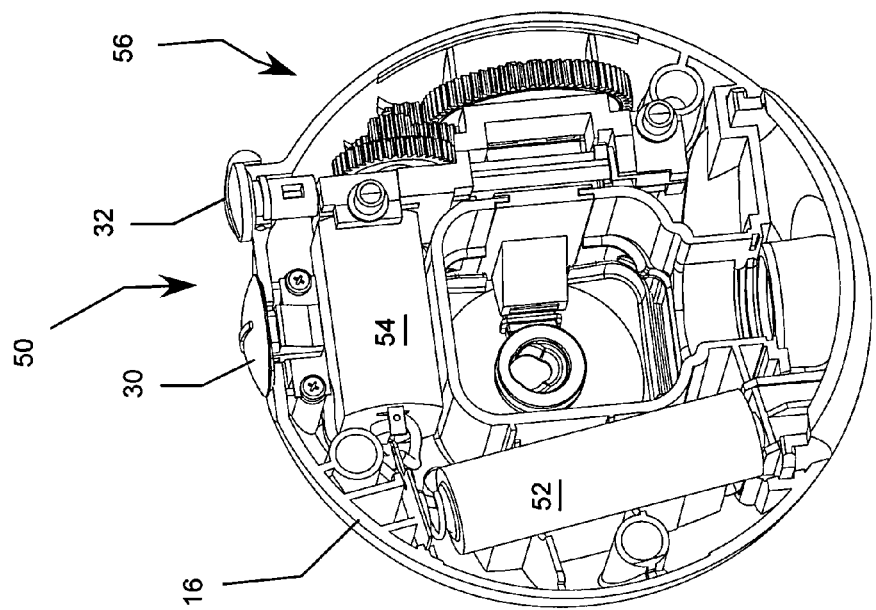
FIG. 10 is a first perspective view of the internal configuration of the breast pump.
Figure 11:
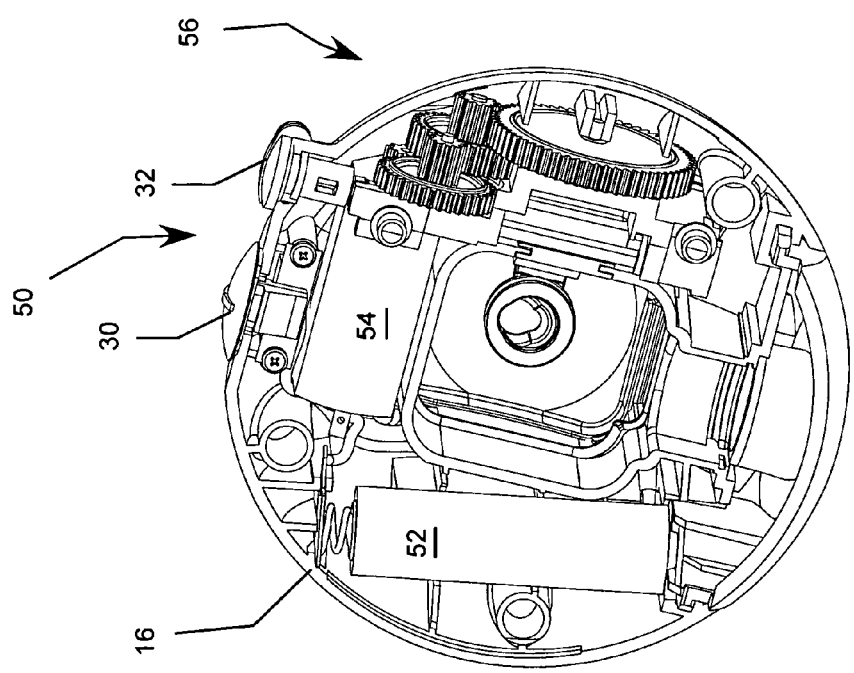
FIG. 11 is a second perspective view of the internal configuration of the breast pump.

FIGS. 10 and 11 are perspective views of the internal configuration of the breast pump 10. These views show the outer housing 16, the power switch control knob 30, and the vacuum adjustment knob 32 located on the exterior of the pump. On the interior of the housing, the breast pump includes a pump mechanism 50 powered by a power source 52, in this embodiment a single AA battery. The pump mechanism 50 includes a motor 54 and a drive train 56, which are shown more clearly in the assembled view of FIG. 12 and the exploded views of FIGS. 13 and 14. The drive train 56, which translates the rotary motion of the motor 54 to reciprocating linear motion of the actuator arm 34, is supported by a motor plate 60 that is attached to the pump housing by a number of shock absorbing bushings for noise reduction. The motor plate 60 supports the motor and includes gear supports 62, 64 and 66 along with slide channels or slots 68 and 70 for receiving the cam follower 72 and actuator arm 34, respectively. The motor 54 drives a pinion gear 80, which engages a drive gear 82 supported by the first gear support 62, which engages a translation gear 84 supported by the second gear support 64, which engages a cam gear 86 supported by the third gear support 66.

The face of the cam gear 86 contains a cam track 90 (shown in FIGS. 24 and 25) that engages a cam follower pin 92 on the cam follower 72 to translate rotary motion of the cam gear into linear motion of the cam follower. The cam follower 72 engages the actuator arm 34 by way of a coil spring 94, which is sufficiently rigid to support the force required to drive the actuator arm when the actuator arm is unconstrained. The cam follower 72 includes a boss 73 that interfaces with the spring 94, which is captured within a spring channel 95 (shown in FIG. 14) of the actuator arm 34. The coil spring 94 compresses to allow the cam follower 72 to move through its range of motion when movement of the actuator arm 34 is constrained. In particular, movement of the actuator arm 34 may be selectively constrained by the cam shaft 96 (shown in FIG. 13) driven by the vacuum adjustment knob 32, which controls the stroke of the actuator arm. The cam shaft 96 has an eccentric cam surface (or may contain multiple flat contact surfaces of varying radius relative to the center of the cam shaft) that blocks a variable amount of the available travel of the actuator arm 34 as the vacuum adjustment knob 32 is rotated.

In addition to providing vacuum adjustment, placement of the coil spring 94 in the drive train linkage between the actuator arm 34 and the cam follower 72 allows the cam follower to continue to reciprocate through its full path of motion even when the actuator arm 34 is manually blocked by another obstruction, for example when the actuator arm is jammed or held down by a person's hand. The coil spring 94 therefore provides stress relief to the drive train and motor, which cannot be manually jammed by blocking the actuator arm. This is a beneficial design feature that avoids potential damage to the pump from jamming the actuator arm, such as stalling and a potential over-current condition that could cause overheating of the motor, stripping of the gears, breaking of the gear supports, bending or breaking of the motor plate, and so forth. The coil spring 94 may also be selected to limit the maximum vacuum that the pump can generate, for example to a maximum limit of 250 mm Hg, which provides a beneficial safeguard against over stressing the mother's breast during pump operation.

Figure 18:
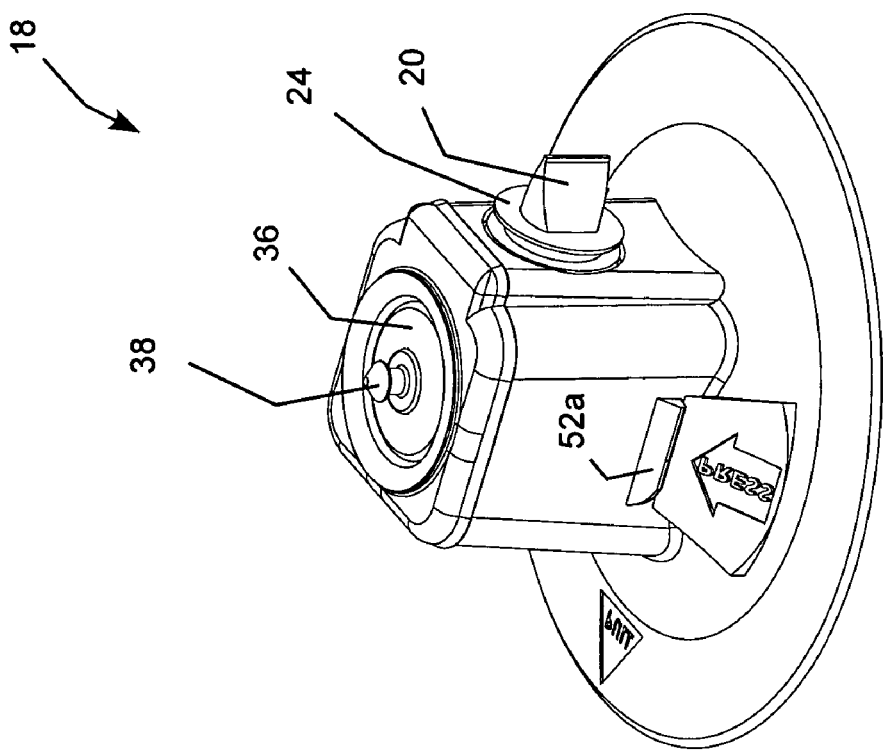
FIG. 18 is a perspective view of the breast cup with the flange top in the inward position.
Figure 17:
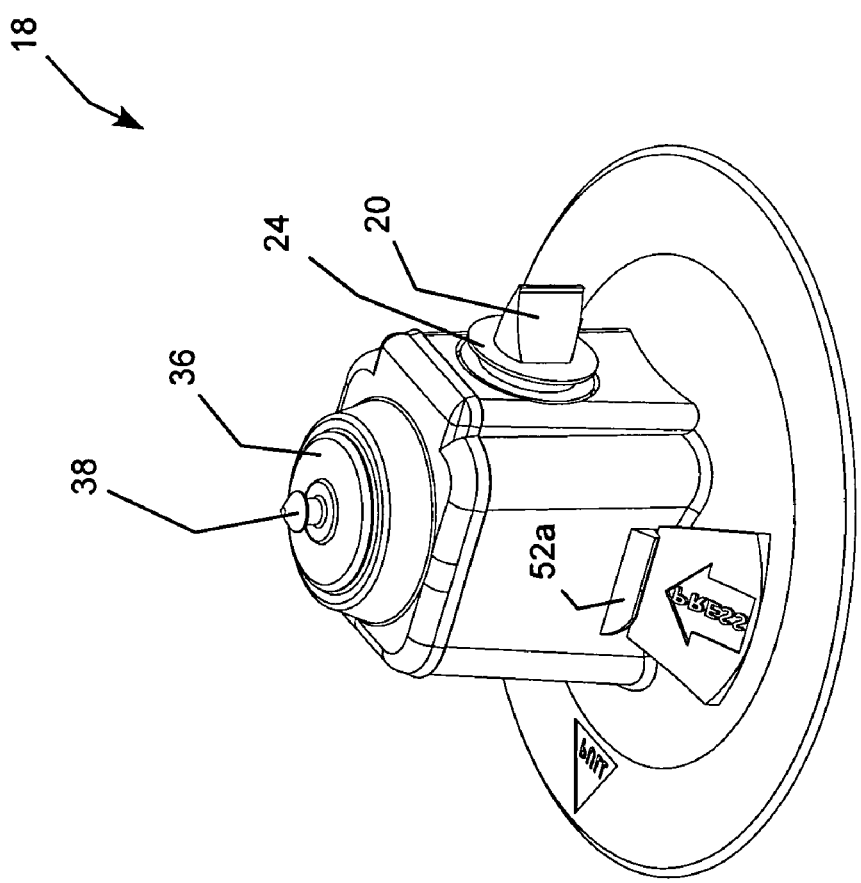
FIG. 17 is a perspective view of the breast cup with the flange top in the outward position.
Figure 20:
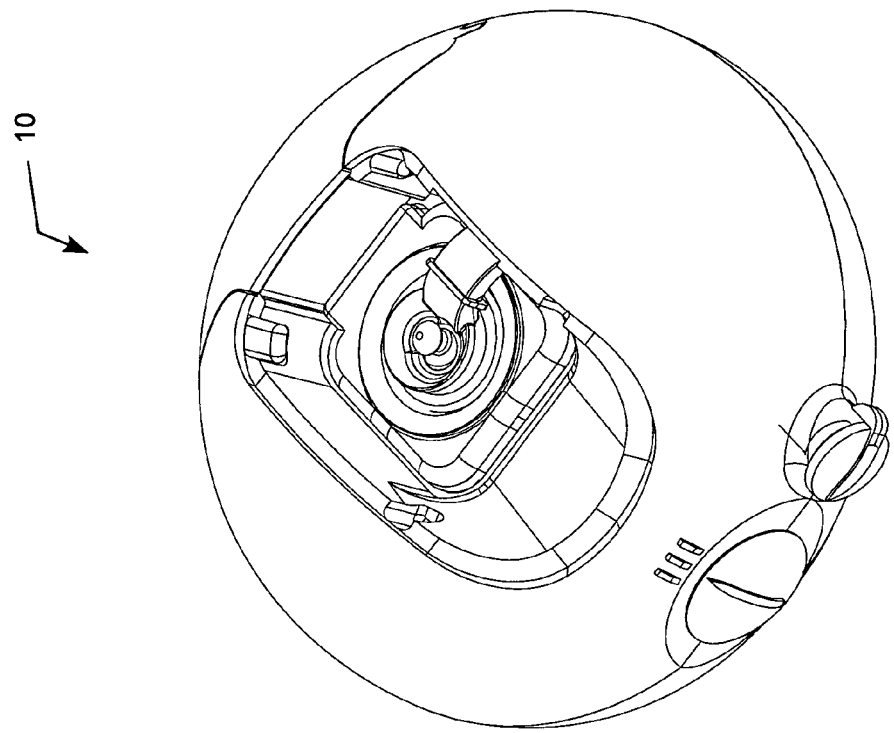
FIG. 20 is a perspective view of the breast pump with an installed breast cup showing the actuator arm and flange top in the inward position.
Figure 19:
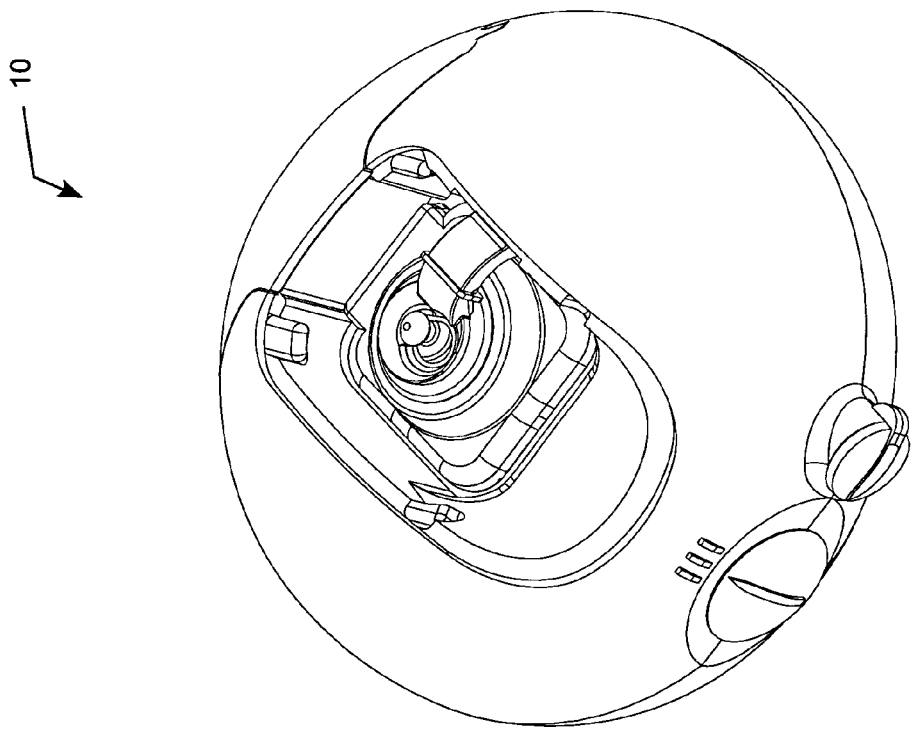
FIG. 19 is a perspective view of the breast pump with an installed breast cup showing the actuator arm and flange top in the outward position.

FIG. 15 is an end view of the breast cup 18 and FIG. 16 is a bottom view of the breast cup showing the bellows structure 42, the nipple tunnel 46, the breast interface section 48, the outer flange area 50, the detent tabs 52*a*-*b*, the outlet 24 that receives the one-way valve, the flange top 36, and the barb 38. FIG. 17 is a perspective view of the breast cup 18 with the flange top 36 and barb 38 in the outward position. This view also shows the one-way valve 20 in its operative position in the outlet 24. FIG. 18 is a perspective view of the breast cup 18 with the flange top 36 in the inward position. FIG. 19 is a perspective view of the breast pump 10 with the breast cup 18 installed showing the actuator arm 34 and flange top 36 in the outward position. FIG. 20 is a perspective view of the breast pump 10 with the breast cup 18 installed showing the actuator arm 34 and flange top 36 in the inward position.

Figure 21:
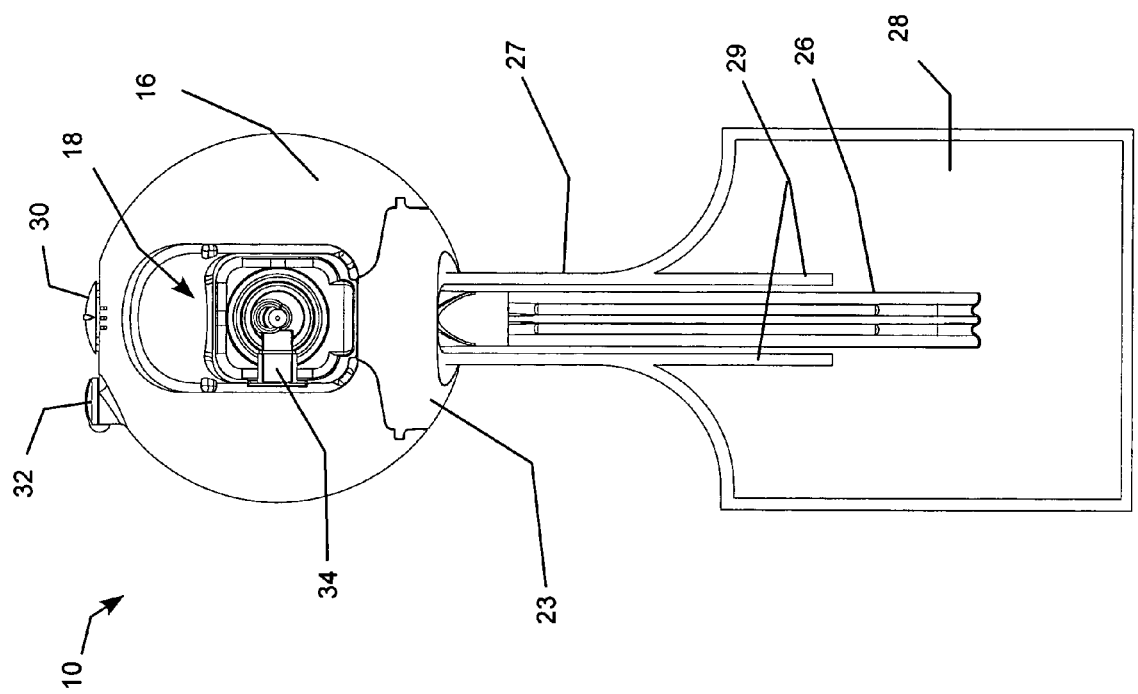
FIG. 21 is a perspective view of the breast pump with the valve, stem and collection bag assembled in their operative positions.

FIG. 21 is a perspective view of the breast pump 10 with the valve 20, stem 26 and collection bag 28 assembled in their operative positions. The collection bag includes an elongated neck 27 that receives the stem 26. The stem as received within the neck of the collection bag extends into an opening in the pump enclosure, where the neck of the collection bag is captured in place between the top portion of the stem and the pump enclosure. The enclosure holds the top portion of the stem against the outlet of the breast cup to provide a leak-free milk transfer path from the outlet 24 of the breast cup to the container portion of the collection bag. As shown in FIG. 1, the stem 26 as received within the elongated neck of the collection bag passes between the bottom of the brassier and the user's chest, such that the container portion or pouch of the collection bag is suspended below and supported by the brassier. The wave shape across the transverse dimension of the stem 26 allows the milk to be transported along the exterior of the stem past the bottom of the brassier even though the stem and the neck of the collection bag are captured between the bottom of the brassier and the user's chest sufficiently firmly to support the container portion of the milk collection bag below the brassier without the aid of hands or other support devices. The collection bag 28 also includes seams 29 that extend from the neck 27 into the container portion of the bag. These seams prevent the collection bag from spilling milk when the collection bag holding milk is laid on its side with the stem 26 removed from the bag. This milk collection system has proven to be very successful in the Gen-1 design, and has therefore been retained in the Gen-2 design with some helpful improvements.

Figure 22:
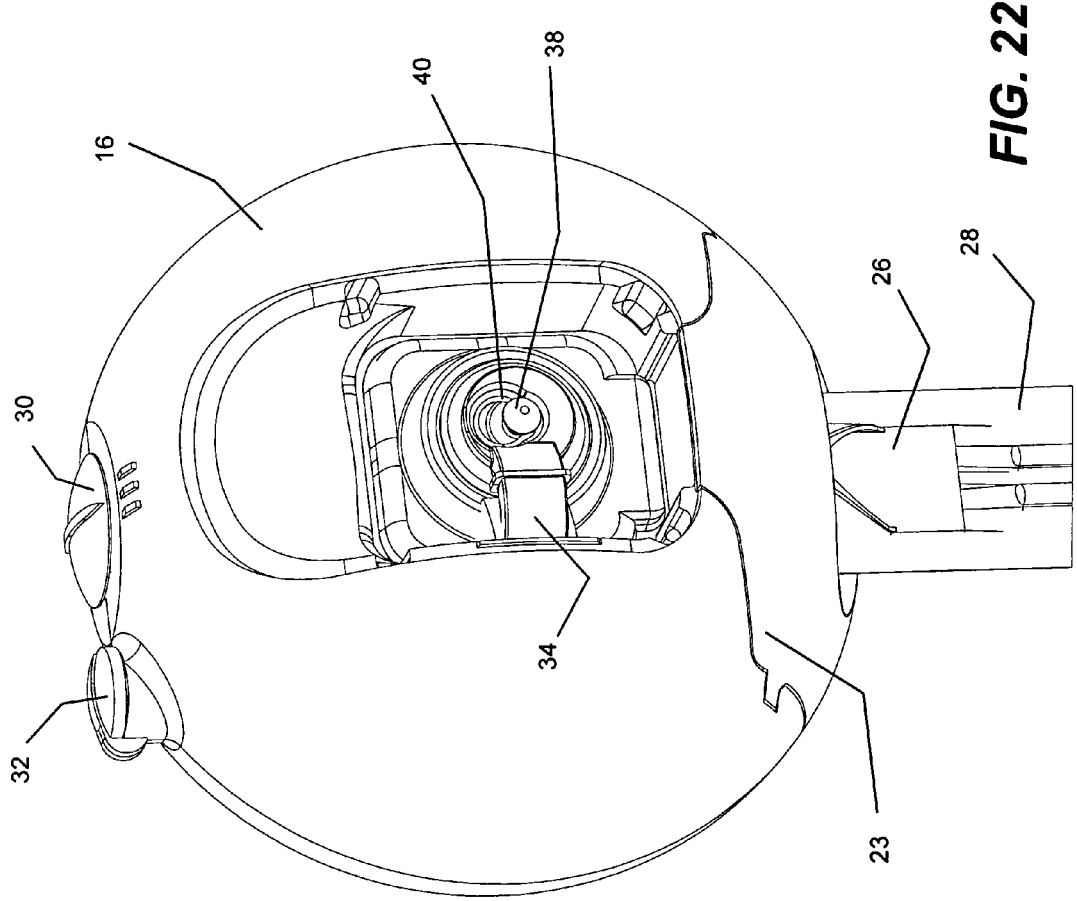
FIG. 22 is another perspective view of the breast pump with the valve, stem and collection bag assembled in their operative positions.

FIG. 22 is another perspective view of the breast pump 10 with the valve 20, stem 26 and collection bag 28 assembled in their operative positions. In FIGS. 21 and 22, the removable cover plate 65 (shown in FIG. 23) that attaches to the outer housing 16 is transparent or removed to reveal the top of the breast cup 18 and its interface with the actuator arm 34. The cover plate 65 may be transparent to allow the user to view the inside of the pump in the area of engagement between the actuator arm and the breast cup when the cover plate is installed. Because the silicon breast cup is also substantially transparent, the user can observe the condition of the nipple and milk flow through the cover plate or window 65, which may also be removable to provide physical access to the area of engagement between the actuator arm and the breast cup. This helps the user observe and adjust the interface between the barb 38 and the detent opening 40 in the actuator arm 34, if necessary, to ensure that the actuator arm is properly engaged with the breast cup. The inner housing 19 of the breast pump may include an additional transparent window on the top of the breast pump enclosure adjacent to the power switch and vacuum control knob allowing the user to view the interface between her breast and the nipple channel of the breast cup from above to aid in proper placement of the breast pump on the breast. If desired, the entire breast pump enclosure may be manufactured from a transparent material to maximize visibility of the internal pump components and to aid in proper placement of the breast pump on the breast.

Figure 23:
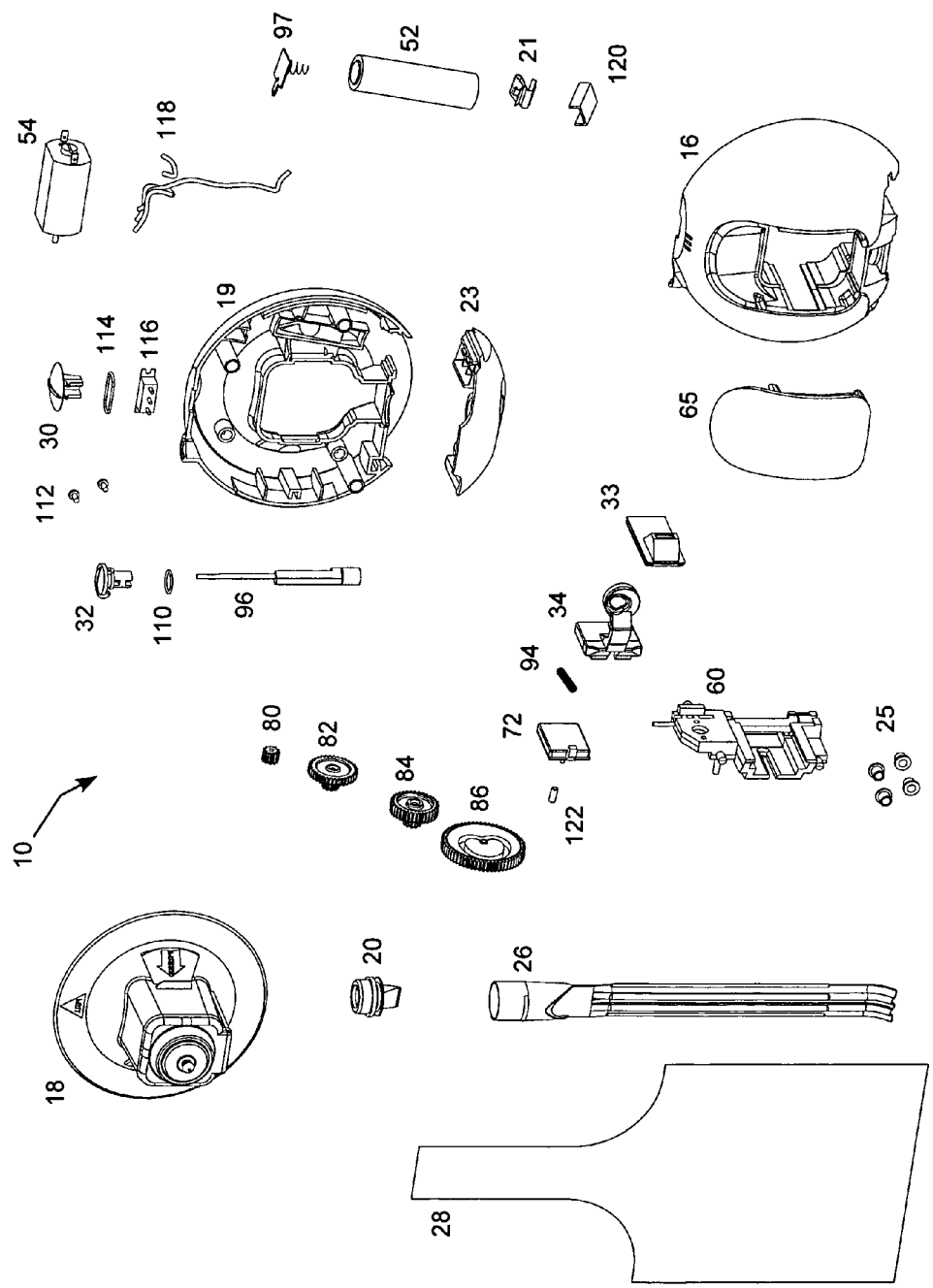
FIG. 23 is a disassembled perspective view of the breast pump showing the major components and accessories.

FIG. 23 is a perspective view of a particular embodiment of the breast pump 10 disassembled showing with the major components and accessories. The accessories of the breast pump include the breast cup 18, the one-way valve 20, the stem 26 and the collection bag 28. The components of the drive train include the motor plate 60, the pinion gear 80, which attaches to the drive shaft of the motor 54, the drive gear 82, the translation gear 84, and the cam gear 86. The gear posts of the motor plate 60 may be cast in the material of the motor plate or they may be inserts, such as stainless steel pins. The cam gear 86 drives the cam follower 72 by way of the cam follower pin 92 (shown in FIGS. 13 and 14), which rides in the cam slot 90 (shown on FIGS. 24 and 25). In this embodiment, the cam follower pin 92 is covered by a sleeve 112, which may be made from NYLON® impregnated with TEFLON® or another suitable material to provide a self-lubricating surface, to reduce friction between the cam slot and the cam follower pin and extend the life of the cam gear. The cam follower 72 is coupled to the actuator arm 34 by way of the coil spring 94.

The hood 33 covers the actuator arm 34 for sound proofing and sealing out liquid or other contaminants. The motor plate 60 is mounted to the pump enclosure by bushings 25 for noise reduction.

The adjustment components of the breast cup include the vacuum control knob 32, which drives the eccentric cam shaft 96. The cam shaft selectively blocks a portion of the stroke of the actuator arm 34 to provide vacuum adjustment, while the coil spring 94 in the linkage between the actuator arm and the cam follower 72 allows the cam follower to move through its full range of motion regardless of the whether a portion of the stroke of the actuator arm is blocked by the cam shaft. A water-tight gasket 110 seals the interface between the vacuum control knob 32 and the housing of the breast pump. The power control knob 30 operates a three-position power control switch 116, which is secured to the housing by screws 112. A water-tight gasket 114 seals the interface between the power control knob 30 and the housing of the breast pump.

The electrical components of the breast cup include the motor 54, the battery 52, and the wiring 118 for electrically connecting the motor the to the battery by way of the switch 116. The battery is electrically connected by way of a spring-type battery terminal 97 that fits into a socket in the pump housing and a leaf-type battery terminal 21 that is supported by a c-channel 120 that fits into a socket in the housing.

The components of the breast pump housing include the inner housing 19 that receives the breast cup 18, the dome-shaped outer housing 16 that faces the inner surface of the breast cup of the user's brassier, and the removable battery cover 23. The outer housing 16 includes a removable (and transparent, if desired) cover plate or window 65. The inner housing 19 may also include a transparent window at the top of the housing below the vacuum control knob 32 and power control knob 30.

Figure 24:
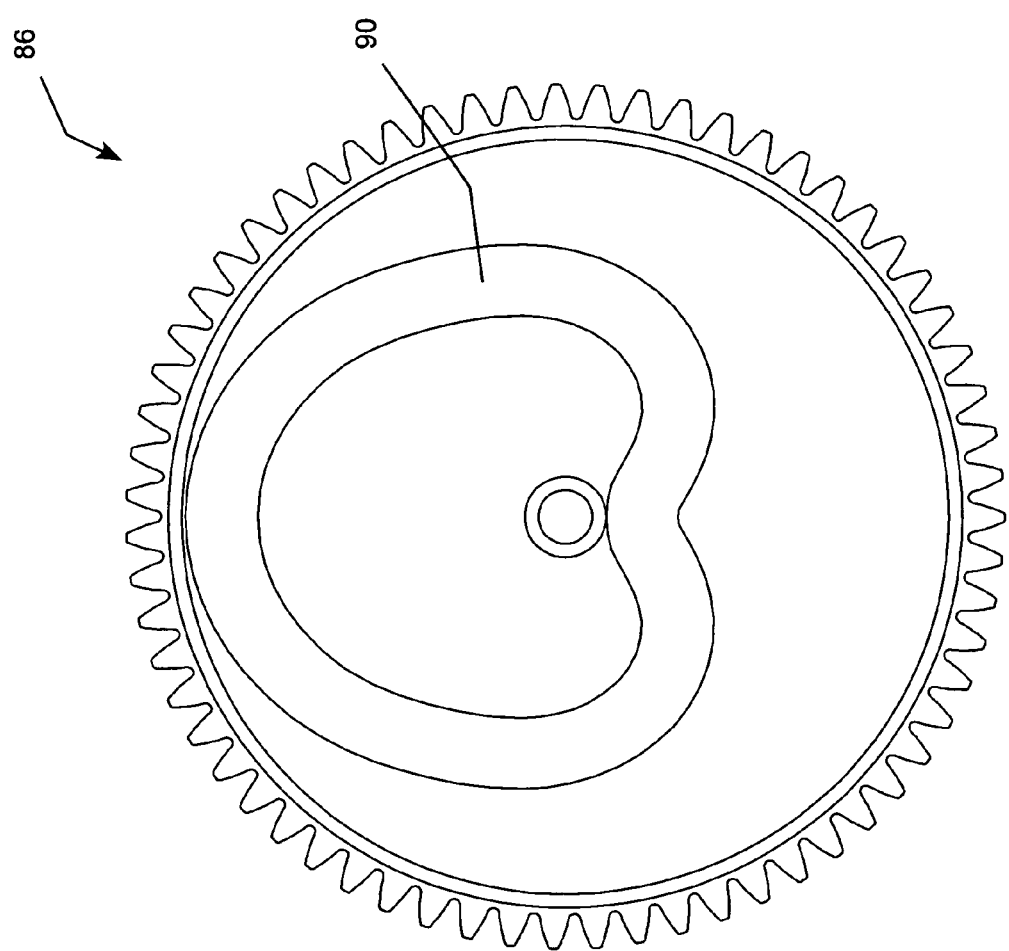
FIG. 24 is a front view of the drive cam of the breast pump.
Figure 25:
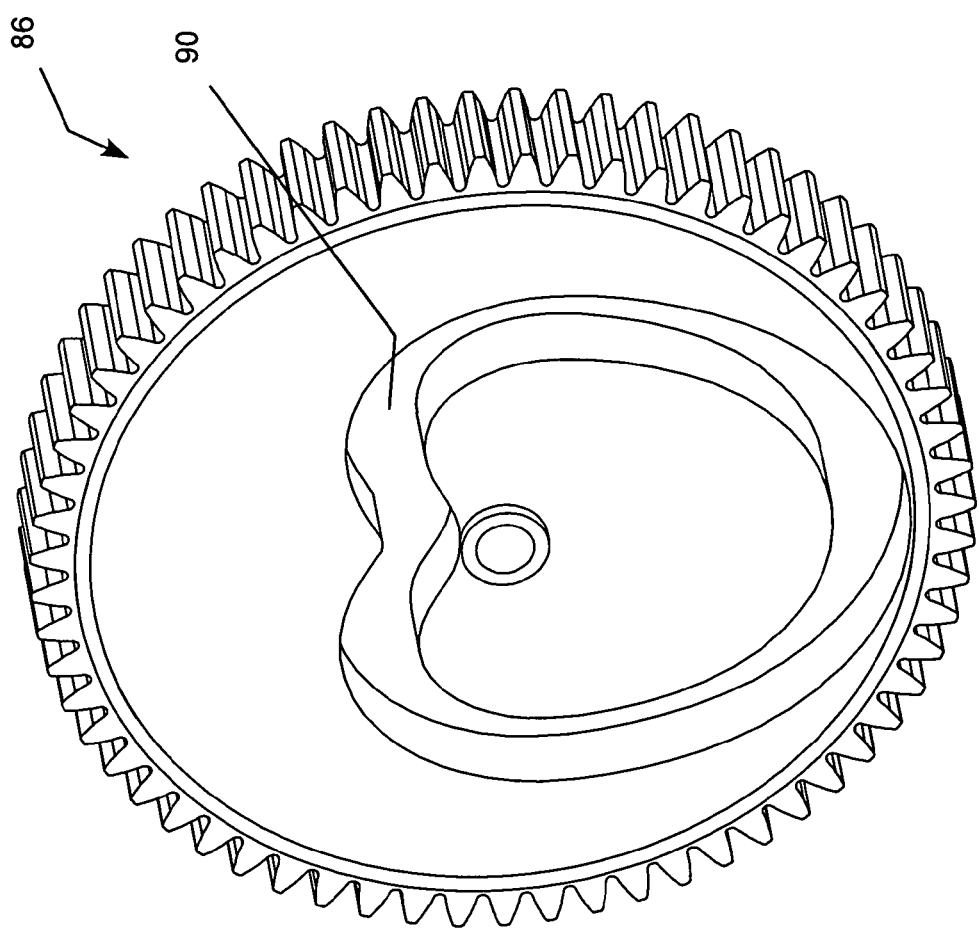
FIG. 25 is a perspective view of the drive cam of the breast pump.
Figure 26:
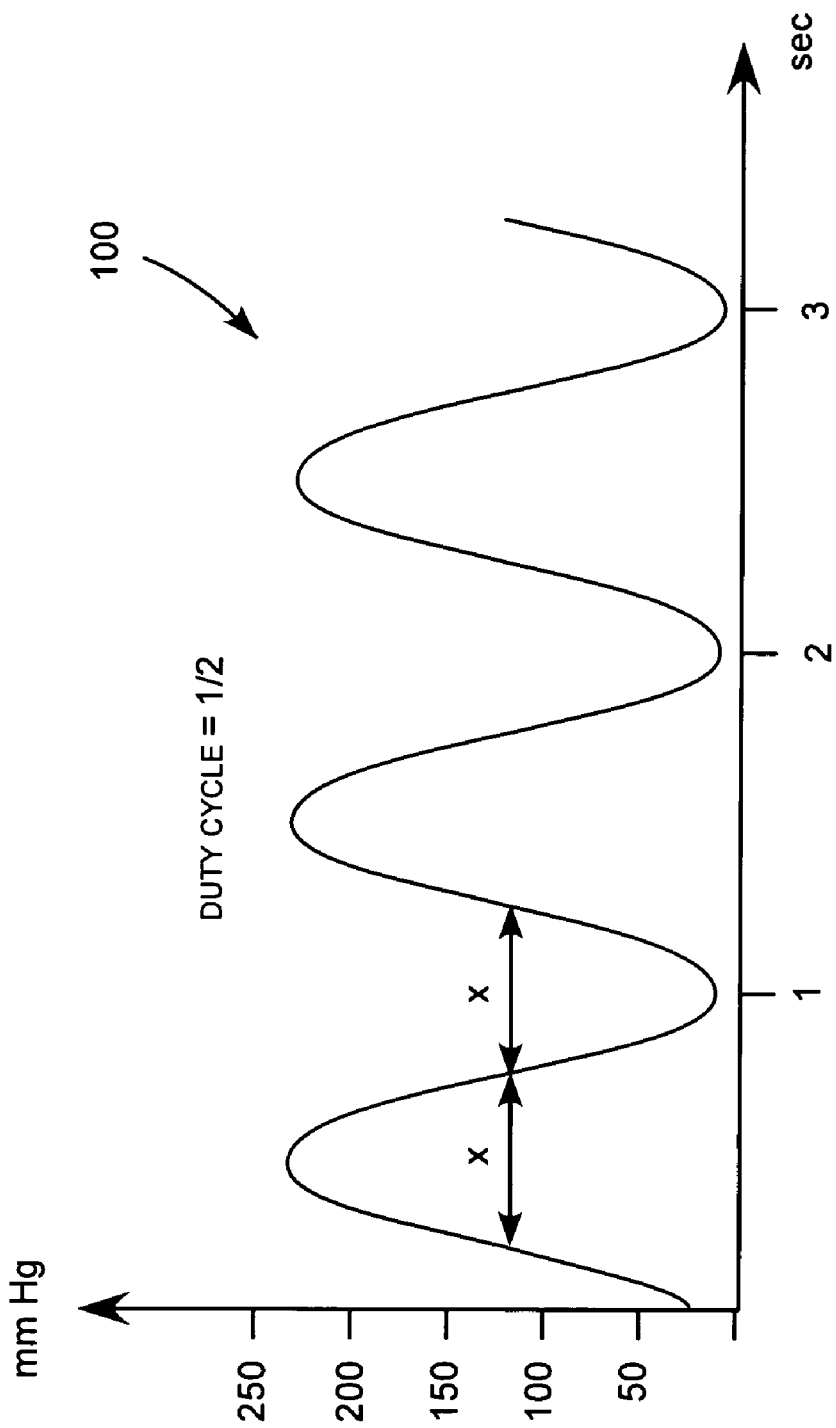
FIG. 26 is an illustrative operating curve for a breast pump with a duty cycle of approximately one-half.
Figure 27:
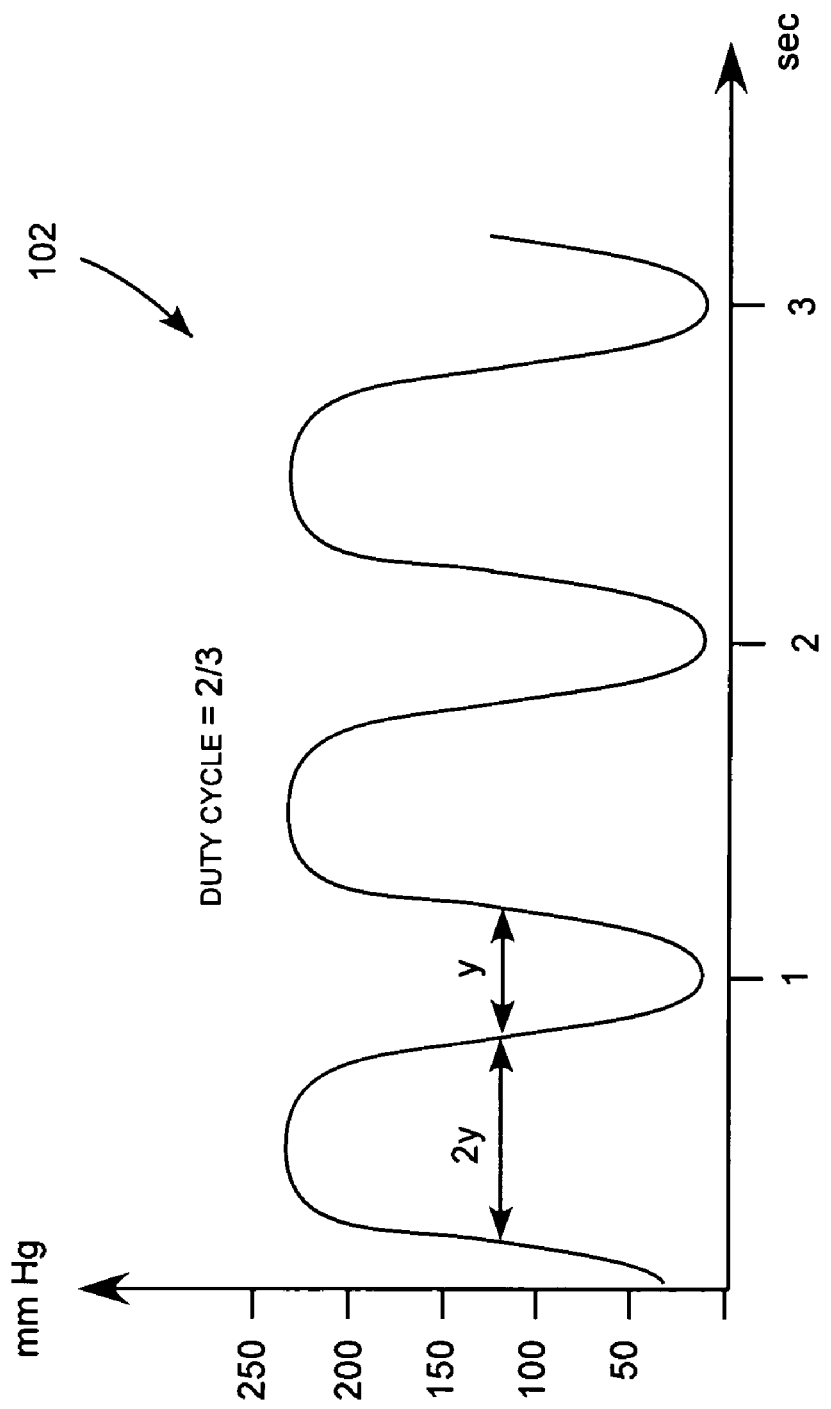
FIG. 27 is an illustrative operating curve for a breast pump with a duty cycle of approximately two-thirds.

FIG. 24 is a front view and FIG. 25 is a perspective view of the cam gear 86 of the breast pump showing the cam track 90, which has a rounded carotid shape to produce the desired pump operating curve. As noted previously, the shape of the cam track 90 can be precisely selected to produce an operating curve with desired characteristics including a desired suck-release ratio or duty cycle. FIG. 26 is an illustrative operating curve 100 for a breast pump with a duty cycle of approximately one-half, and FIG. 27 is an illustrative operating curve 102 for a breast pump with a duty cycle of approximately two-thirds. The operating curve 100 has a suck-release ratio of approximately 1:1 (i.e. suck time=x, release time=x), whereas the operating curve 102 has a suck-release ratio of approximately 2:1 (i.e. suck time=2y, release time=y), as indicated in the figures. Referring to FIGS. 24 and 25, the shape of the operating curve 100, 102 is controlled by the shape of the cam track 90 and can be adjusted by changing the shape of the cam track within the operating capability of the motor and gear train. The dynamic properties of the gear train and the bellows structure of the breast cup also affect the performance of the breast pump.

Referring to FIGS. 26 and 27 with further reference to the breast cup shown in FIGS. 8, 9A-B and 15-18 and the shape of the cam track shown in FIGS. 24 and 25, the performance of the breast pump is generally optimized by designing the breast cup with a high degree of balance in the drive train so that the bellows structure 42 of the breast cup 18 requires about the same amount of force during the inward stroke as during the outward stroke during normal operating conditions. Up to 250 mm Hg of negative pressure is generated on the outward stroke (when the one-way valve is closed) while only a small level of positive pressure is required on the inward stroke (when the one-way valve is open) to evacuate the expressed milk through the one-way valve and into the collection bag. On the other hand, the silicon of the bellows structure resists the inward stroke and assists in the outward stroke as the bellows resiliently returns to its original shape. That is, the bellows structure acts like a spring that is charged during the inward stroke and discharged during the outward stroke. Given this configuration, the performance of the breast pump is generally optimized when the bellows structure requires about the same maximum amount of force during the inward stroke as during the outward stroke under normal operating conditions, which results in minimum peak power consumption and a relatively steady current profile for the motor.

Although precise power optimization is not required for the pump to operate acceptably, taking the pumping dynamics into account allows the engineer to select among the available design parameters to obtain an efficient pump design that meets the basic design criteria of the breast pump. The design objectives include a maximum suction close to but not more than 250 mm Hg, and maximum suction in the range of 210 to 240 mm Hg is expected to produce acceptable results. An operating profile with a duty cycle of about two-thirds is considered to be desirable because this profile is generally consistent with the measured suck-release profile of a live nursing baby, and operating profiles with duty cycles in the one-half to two-thirds range are expected to produce acceptable results. The pump should operate at about 60 cycles per second to be roughly consistent with a nursing baby, and cycle rates in the range of 45 to 65 cycles are expected to produce acceptable results. Experience with the Gen-2 design confirm that the embodiments described in this application meet these design criteria and perform acceptably on live nursing adult women.

More specifically, these design objectives can be achieved using the breast cup profile shown in FIGS. 8, 9A-B and 15-18 manufactured from 50 durometer silicon, the shape of the cam track shown in FIGS. 25 and 26 producing a linear stroke of the actuator arm in the range of approximately 7.5-8.5 mm, and a motor driven by a single 1.5 Volt AA battery. For this particular embodiment of the breast pump, the motor may be rated for 2.4 Volts DC and 7,700 rpm (e.g., Mabuchi FF-180SH motor). The operating speed of the motor is a function of the load applied to the motor and can be further controlled by adjusting the applied voltage through the range of about 1.0 to 1.5 Volts, for example through the use of a resistive voltage divider or voltage limiting diodes. Vacuum adjustment can be controlled with a cam shaft that selectively blocks and thereby controls the stroke of the actuator arm in the range of about 6 to 8 mm. The coil spring in the drive train between the cam follower and the actuator arm should be selected to limit the suction that can be developed by the breast cup to be no greater than about 250 mm Hg.

Figure 28:
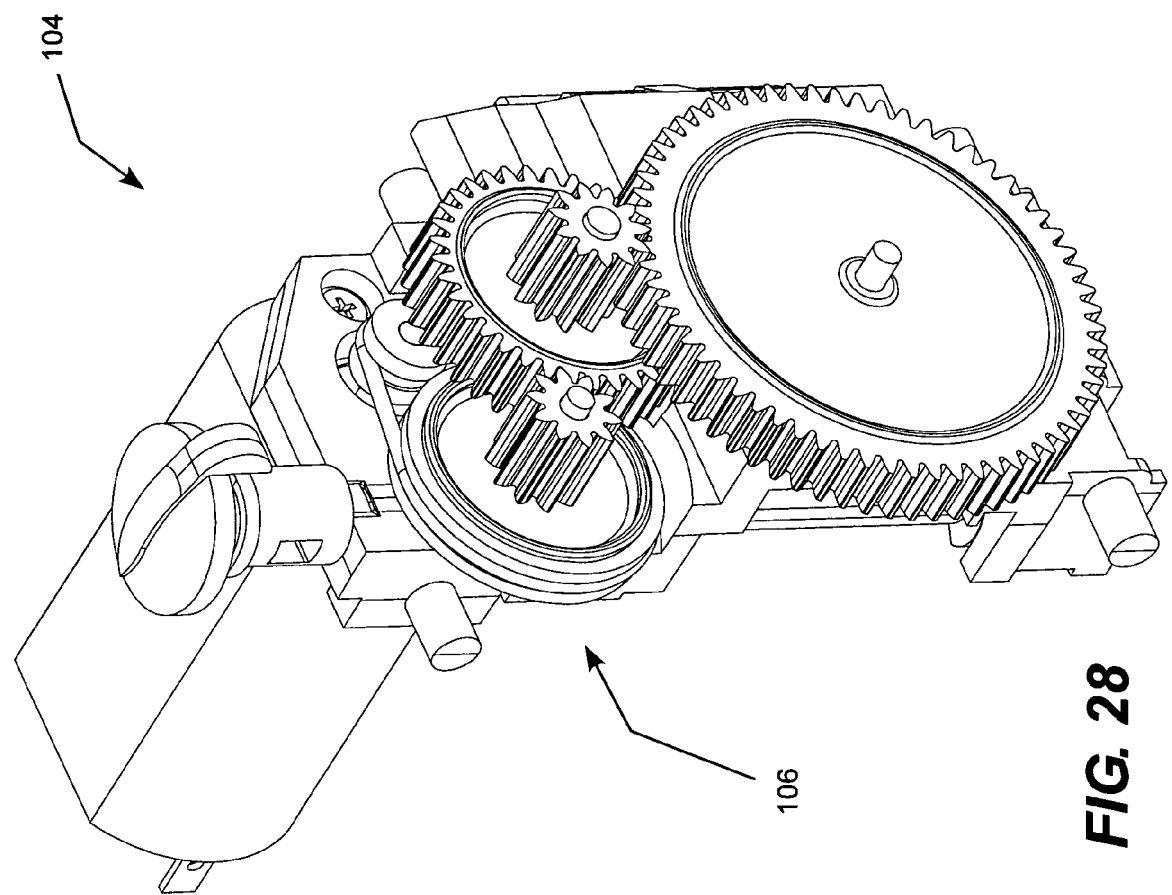
FIG. 28 is an assembled perspective view of a modified drive train for the breast pump that includes a belt drive.

The operating noise of the pump can be mitigated by using a relatively soft material, such as a 50 durometer urethane, for the drive gear. As shown in FIG. 28, the mesh between the pinion gear and the drive gear may also be replaced by a belt drive if further noise mitigation is desired. The other gears may also be 50 durometer urethane, or they may be manufactured from NYLON® or another suitable material. Manufacturing the gears from a self lubricating material, such as NYLON® impregnated with TEFLON® is also desirable. The gear teeth should be shaped to minimize chatter in the drive train, as shown in the applicable figures, and the gears can be machine cut, injection molded, or manufactured with another suitable process. The housing can be made of any material suitable for injection molding the desired shape exhibiting acceptable strength and durability, such as LEXAN®.

The motor plate may be manufactured from a similar material, such as LEXAN®, and the gear support posts may be cast as part of the motor plate or they may be metal inserts, such as stainless steel pins. The bushings at the attachment points between the motor plate and the housing can be made of rubber or a synthetic material such as NEOPRENE® or any other material suitable for this purpose. It is important that the motor plate be sufficiently rigid to prevent bending in a manner that constricts the slide channels or slots where the cam follower and actuator arm slide, as this could result in binding. To prevent binding, the slide channels may be reinforced with metal inserts, such as stainless steel, to provide increased rigidity. The actuator arm and cam follower may be ULTEM®, NYLON® or another suitable material, and a self lubricating material, such as NYLON impregnated with TEFLON®, is also desirable for these components. The pin of the cam follower may be cast as part of the cam follower. The cam follower pin may be covered by a sleeve made from a suitable material, such as stainless steel, or the may be a metal insert, such as a stainless steel pin. The cam follower pin may carry a sleeve made of NYLON impregnated with TEFLON® or similar material to reduce friction between the cam follower pin and the cam slot of the cam gear during normal operation of the pump.

FIG. 28 shows an assembled perspective view of a modified drive train 104 for the breast pump that includes a belt drive 106 between the motor-driven gear and the main drive gear. The belt drive further mitigated noise produced by the drive train.

In view of the foregoing, it will be appreciated that present invention provides significant improvements in breast pumps. It should be understood that the foregoing relates only to the exemplary embodiments of the present invention, and that numerous changes may be made therein without departing from the spirit and scope of the invention as defined by the following claims.

The invention claimed is:

1. A breast pump comprising:
   a housing supporting a pump mechanism operative for reciprocal movement through an inward pump stroke and an outward pump stroke;
   a breast cup configured to be supported by the housing in engagement with the pump mechanism comprising an interface section configured to form an air-tight seal with an adult human breast received against the interface section;
   the breast cup defining a bellows structure;
   the breast cup and the breast creating a vacuum chamber configured to reduce in volume when the bellows structure is compressed during the inward pump stroke and to increase in volume when the bellows structure is expanded during the outward pump stroke;
   the breast cup further comprising an outlet for expelling breast milk expressed from the breast;
   a one-way valve operative to vent the vacuum chamber to allow the milk to pass through the outlet when the vacuum chamber is compressed during the inward pump stroke to create positive pressure within the vacuum chamber, the one-way valve further operative for sealing the vacuum chamber when the vacuum chamber is expanded during the outward pump stroke to create negative pressure within the vacuum chamber, thereby creating a milking action for causing milk to be expressed from the breast;
   wherein the pump mechanism comprises a balanced drive system configured to apply force to compress the vacuum chamber during the inward pump stroke and to apply force to expand the vacuum chamber during the outward pump stroke;
   further comprising a motor and cam gear for translating rotary motion of the motor to linear reciprocating motion of an actuator arm that removably engages with the breast cup for pushing the bellows structure to compress the vacuum chamber during the inward pump stroke and pulling the bellows structure to expand the vacuum chamber during the outward pump stroke; and
   wherein the housing and breast cup are sized and configured to be supported between the adult human breast and a breast cup of a brassier while the breast pump is actively pumping milk from the breast and expelling the milk through the outlet.

2. The breast pump of claim 1, wherein the cam gear defines a cam track and the actuator arm comprises a cam follower captured with the cam track for creating a vacuum profile within the vacuum chamber comprising a repeating pattern having a suck time and a release time in which the suck time is greater than the release time.

3. A breast pump of claim 1, wherein the housing and breast cup are sized and configured to be supported by the brassier without the aid of hands or other support devices.

4. The breast pump of claim 3, wherein the housing is configured to receive an electric battery for delivering electric power to the pump mechanism.

5. The breast pump of claim 4, wherein the housing is configured to receive an electric power cord for delivering electric power to the pump mechanism.

6. The breast pump of claim 1, wherein the vacuum chamber comprises a resilient bellows structure that resists the force applied by the pump mechanism during the inward stroke and assists the force applied by the pump mechanism during the outward.

7. The breast pump of claim 6, wherein the force applied by the pump mechanism in normal operation during the inward stroke is within eighty percent of the force applied by the pump mechanism during the outward stroke.

8. The breast pump of claim 1, wherein the one way valve is removably received within the outlet of the breast cup.

9. The breast pump of claim 1, wherein the breast cup is removably received within the housing.

10. The breast pump of claim 2, wherein the suck time is approximately twice the release time.

11. A breast pump comprising:
    a housing supporting a pump mechanism operative for reciprocal movement through an inward pump stroke and an outward pump stroke;
    a breast cup configured to be supported by the housing in engagement with the pump mechanism comprising an interface section configured to form an air-tight seal with an adult human breast received against the interface section;
    the breast cup and the breast creating a vacuum chamber configured to reduce in volume when compressed during the inward pump stroke and to increase in volume when expanded during the outward pump stroke;
    the breast cup further comprising an outlet for expelling breast milk expressed from the breast;
    a one-way valve operative to vent the vacuum chamber to allow the milk to pass through the outlet when the vacuum chamber is compressed during the inward pump stroke to create positive pressure within the vacuum chamber, the one-way valve further operative for sealing the vacuum chamber when the vacuum chamber is expanded during the outward pump stroke to create negative pressure within the vacuum chamber, thereby creating a milking action for causing milk to be expressed from the breast;

wherein the pump mechanism comprises a balanced drive system configured to apply force to compress the vacuum chamber during the inward pump stroke and to apply force to expand the vacuum chamber during the outward pump stroke;

further comprising a motor and cam gear for translating rotary motion of the motor to linear reciprocating motion of an actuator arm that removably engages with the breast cup, pushes a bellows structure to compress the vacuum chamber during the inward pump stroke and pulls the bellows structure to expand the vacuum chamber during the outward pump stroke; and further comprising a vacuum adjustment mechanism operative to selectively block a portion of the motion of the actuator arm to adjust the length of the inward and outward pump strokes to adjust the amount of negative pressure generated by the vacuum chamber.

12. The breast pump of claim 11, further comprising a spring linkage in a drive train between the cam gear and the actuator arm permitting the vacuum adjustment mechanism to selectively block a portion of the motion of the actuator arm without blocking rotation of the cam gear.

13. The breast pump of claim 12, wherein the vacuum adjustment mechanism comprises a cam shaft having an eccentric cam surface that selectively blocks a varying amount of the motion of the actuator arm in response to rotation of the cam shaft.

14. The breast pump of claim 1, wherein the housing comprises a transparent window facilitating viewing a nipple of a user's breast when the breast is received against the interface section of the breast cup.

15. The breast pump of claim 1, further comprising a milk collection container for collection milk expelled from the breast cup.

16. The breast pump of claim 15, wherein the milk collection container comprises a milk collection bag comprising an elongated neck and a container portion in fluid communication with the neck.

17. The breast pump of claim 16, further comprising a milk conduit having a coupling end in fluid communication with the outlet of the breast cup and a stem section received within the elongated neck of the collection bag, wherein the brassier supports the housing, the breast interface flange, the milk conduit, and the milk collection bag without the aid of hands or other support devices.

18. The breast pump of claim 17, wherein the milk conduit received within the elongated neck of the collection bag is configured to pass between a lower edge of the brassier and the body of a user wearing the brassier.

19. The breast pump of claim 18, wherein the stem section of the milk conduit defines an elongated dimension and a narrow dimension, and the stem section defines an open wave shape across the narrow dimension.

20. The breast pump of claim 16, wherein the container portion of the milk collection bag comprises first and second side panels and the milk collection bag comprises one or more seams sealing the first and second side panels together within part of the container portion of the milk collection bag to prevent milk contained within the container portion from leaking through the elongated neck when the milk collection bag is laid down horizontally on the first or second side panel without the milk conduit received within the elongated neck.

* * * * *